(12) United States Patent
King et al.

(10) Patent No.: US 10,881,712 B2
(45) Date of Patent: Jan. 5, 2021

(54) NEUROPROTECTIVE AGENTS DERIVED FROM SPIDER VENOM PEPTIDES

(71) Applicants: THE UNIVERSITY OF QUEENSLAND, Brisbane (AU); MONASH UNIVERSITY, Clayton (AU)

(72) Inventors: Glenn Frederick King, Chapel Hill (AU); Lachlan Douglas Rash, Anstead (AU); Irene Chassagnon, Highgate Hill (AU); Sandy Steffany Pineda Gonzalez, Rochedale (AU); Robert Edward Widdop, Malvern East (AU); Claudia Ann Ireland, Aspendale (AU)

(73) Assignees: The University of Queensland, Brisbane (AU); Monash University, Clayton (AU)

(*) Notice: Subject to any disclaimer, the term of this patent is extended or adjusted under 35 U.S.C. 154(b) by 0 days.

(21) Appl. No.: 16/599,788

(22) Filed: Oct. 11, 2019

(65) Prior Publication Data
US 2020/0061156 A1 Feb. 27, 2020

Related U.S. Application Data

(63) Continuation of application No. 15/745,432, filed as application No. PCT/AU2016/050633 on Jul. 18, 2016, now Pat. No. 10,485,847.

(30) Foreign Application Priority Data

Jul. 17, 2015 (AU) ............................... 2015902845

(51) Int. Cl.
| | | |
|---|---|---|
| *C07K 14/435* | (2006.01) | |
| *A61P 25/28* | (2006.01) | |
| *A61P 25/08* | (2006.01) | |
| *A61P 9/14* | (2006.01) | |
| *A61K 38/17* | (2006.01) | |
| *A61K 9/00* | (2006.01) | |
| *A61P 9/10* | (2006.01) | |
| *A61K 38/00* | (2006.01) | |

(52) U.S. Cl.
CPC ........ *A61K 38/1767* (2013.01); *A61K 9/0019* (2013.01); *A61K 9/0043* (2013.01); *A61K 9/0085* (2013.01); *A61P 9/10* (2018.01); *A61P 9/14* (2018.01); *A61P 25/08* (2018.01); *A61P 25/28* (2018.01); *C07K 14/43518* (2013.01); *A61K 38/00* (2013.01); *C07K 2319/23* (2013.01); *C07K 2319/24* (2013.01); *C07K 2319/50* (2013.01)

(58) Field of Classification Search
None
See application file for complete search history.

(56) References Cited

U.S. PATENT DOCUMENTS

| 5,281,693 A | 1/1994 | Jackson et al. |
| 2015/0148288 A1 | 5/2015 | Kennedy et al. |
| 2018/0207235 A1 | 7/2018 | King et al. |

FOREIGN PATENT DOCUMENTS

| WO | WO01/85931 A2 | 11/2001 |
| WO | WO2007030580 A2 | 3/2007 |
| WO | WO2008/061329 A2 | 5/2008 |
| WO | WO2013/134734 | 9/2013 |

OTHER PUBLICATIONS

International Search Report for PCT/AU2016/050633, five pages (dated Sep. 2016).
Written Opinion of the ISA for PCT/AU2016/050633, eight pages (dated Sep. 2016).
Bohlen et al. "A bivalent tarantula toxin activates the capsaicin receptor, TRPV1, by targeting the outer pore domain" *Cell*, vol. 141, No. 5, pp. 834-845 (May 2010).
Bohlen et al. "A heteromeric Texas coral snake toxin targets acid-sensing ion channels to produce pain" *Nature*, vol. 479, No. 7373, pp. 410-414 (Nov 2011).
Rodriguez et al. "A novel sea anemone peptide that inhibits acid-sensing ion channels" *Peptides*, vol. 53, pp. 3-12 (Mar. 2014).
Vassilevski et al. "Novel class of spider toxin: Active principle from the yellow sac spider *Cheiracanthium punctorium* venom is a unique two-domain polypeptide" *Journal of Biological Chemistry*, vol. 285, No. 42, pp. 32293-32302 (Oct. 2010).
Extended European Search Report mailed in EP Appl. No. 16826924.9 (12 pages) dated Feb. 26, 2019.
Chassagnon, IR et al: "Potent neuroprotection after stroke afforded by a double-knot spider-venom peptide that inhibits acid-sensing ion channel 1a". Proceedings of the National Academy of Sciences of the United States of America. 114(14): 3750-3755, Mar. 20, 2017.
Maxwell, M et al., "Secreted Cysteine-Rich Repeat Proteins "SCREPs": A Novel Multi-Domain Architecture" Frontiers in Pharmacology. vol. 9. Article 1333, Nov. 20, 2018.
Unknown, "Tarantula psalmotoxin 1 PcTx peptide SEQ ID No. 8." retrieved from EBI accession No. GSP:AFH53532, Jul. 26, 2007.
Unknown, "Sequence 6 from Patent W02007030580" retrieved from EBI accession No. EPOP:GM000690, Nov. 20, 2008.
Kim et al., A Chemically Cross-Linked Knottin Dimer Binds Integrins with Picomolar Affinity and Inhibits Tumor Cell Migration and Proliferation, J. Am. Chem. Soc. 137:6-9; Dec. 8, 2014.
Saez et al., Spider-Venom Peptides as Therapeutics, Toxins 2:2851-2871; doi:10.3390/toxins2122851 (2010).

*Primary Examiner* — John D Ulm
(74) *Attorney, Agent, or Firm* — Nixon & Vanderhye, PC

(57) ABSTRACT

The invention relates to disulfide-rich peptides derived from spider venom and their use, particularly as neuroprotective agents. The invention also relates to nucleic acid molecules encoding the peptides as well as constructs and host cells comprising those nucleic acid molecules.

20 Claims, 16 Drawing Sheets

Specification includes a Sequence Listing.

```
         1              10                20                30                40                50                60                70
Hila  NECIRKWLSCVDRKMDCCEGLECYKRRHSFEVCVPIPG---FCLVKWKQDGRERDCCAGLECWKRSGNKSSVCAPIT   75
Hilb  NECIRKWLSCVDRKMDCCEGLECYKRRHSFEVCVPIPG---FCLVKWKQDGRERDCCAGLECWKRSGNKSSVCAPIT   75
Hilc  QECIRKWKSCARKIDCCEGLECWKRRWGHEVCVPITGKTHLFCKTHKIKKYKDCFERKIDCCRELECWERRGNKEEVCAPKQ 77
Hild  QECIARMKSCAGRKIDCCEGLECWKRRWGHEVCVPITGKI-FCLEKRWKSCFRKIDCCRELECWERRGNKEEVCAPKQ  77
Hile  NECIRKWLSCVDRKMDCCEGLECYKRRHSFEVCVPIPG---FCLVKWKQDGRERDCCAGLECWKRSGNKSSVCAPIA   75

80              90              100
                                                                                        SKATHHPKVKRSYSCHER SKATHHTC            100
```

Figure 1

```
Hi1a    NECIRKWLSCVDRKNDCCEGLECYKRRHSFEVCVPIPG--FCLVKWKQCDGRERDCCAGLECWKRSGNKSSVCAPIT  75
Hi1d    QECIAKWKSCAGRKLDCCEGLECWKRRWGHEVCVPITQKIFCLEKWKSCFERKYDCCEELECWERRGNKHPVCAPKQ  77
```

NEUROPROTECTIVE AGENTS DERIVED FROM SPIDER VENOM PEPTIDES

CROSS-REFERENCE TO RELATED APPLICATIONS

This application is a Continuation of U.S. application Ser. No. 15/745,432, 371(c) date Jan. 16, 2018, which is the U.S. national phase of International Application No. PCT/AU2016/050633, filed Jul. 18, 2016, which designated the U.S. and claims priority to Australian Patent Application No. 2015902845, filed Jul. 17, 2015; the entire contents of each of which are hereby incorporated by reference.

REFERENCE TO A SEQUENCE LISTING SUBMITTED ELECTRONICALLY VIA EFS-WEB

The content of the electronically submitted sequence listing (Name: 0181_0444_amended_Sequence_Listing.TXT, Size: 34,547 bytes; and Date of Creation: Oct. 31, 2019) is herein incorporated by reference in its entirety.

TECHNICAL FIELD

The present invention relates to disulfide-rich peptides derived from spider venom and their use, particularly as neuroprotective agents. More particularly, in one aspect, the invention relates to disulfide-rich peptides that have neuroprotective activity following stroke as well as to compositions containing such peptides and their use in the treatment of stroke. The invention also relates to nucleic acid molecules encoding the peptides as well as constructs and host cells comprising those nucleic acid molecules.

BACKGROUND ART

Stroke is the second leading cause of death worldwide (Woodruff et al., 2011; Moskowitz et al., 2010), and the third leading cause of mortality in Australia (Senes, 2006). In addition to the high rate of mortality, there is an extremely high incidence of morbidity in stroke survivors, making it the leading cause of disability in industrialised countries (Liu et al., 2012).

Within a few minutes of the onset of cerebral ischemia, the infarct core is mortally injured and undergoes necrotic cell death. The infarct core (or striatal region) of the stroke is commonly considered unsalvageable. The necrotic core is surrounded by a zone of less severely affected tissue known as the ischemic penumbra or peri-infarct zone, which is potentially salvageable via post-stroke therapy (Woodruff et al., 2011). The use of recombinant tissue plasminogen activator (rtPA) to help restore blood flow to the ischemic region is, to date, the only approved agent for treatment of acute ischemic stroke. It is used in only 3-4% of all stroke patients (Besancon et al., 2008) due to its narrow therapeutic window and the risk of inducing intracranial haemorrhage (Moskowitz et al., 2010). There is clearly a need for more effective neuroprotective agents. A longer time window for therapeutic intervention would also be advantageous.

During cerebral ischemia, severe oxygen depletion occurs, compelling the brain to switch from oxidative phosphorylation to anaerobic glycolysis, leading to acidosis as a result of increased lactate levels. The extracellular pH can fall from ~7.3 to 6.0-6.5 in the ischemic core under normoglycemic conditions, and can drop to below 6.0 during severe ischemia (Xiong et al., 2004; Isaev et al., 2008). The drop in extracellular pH activates acid sensing ion channels (ASICs), and activation of these channels is thought to play a critical role in stroke-induced neuronal injury. Numerous studies have demonstrated a direct correlation between brain acidosis and infarct size (Xiong et al., 2007).

ASICs were discovered in the late 1990s, almost 20 years after the observation that sensory neurons depolarise in response to a sudden drop in pH (Krishtal, 2003). Although they belong to the epithelial sodium channel/degenerin family of receptors, they are distinguished by their restriction to chordates, predominantly neuronal distribution, and activation by decreases in extracellular pH (Gründer and Chen, 2010). Alternative splicing of four ASIC-encoding genes leads to the expression of six subunits (ASIC1a, ASIC1b, ASIC2a, ASIC2b, ASIC3 and ASIC4) that combine to form hetero- or homo-trimeric channels that differ in their pH sensitivity, kinetics, and susceptibility to desensitisation (Wemmie et al., 2006).

Postsynaptic ASIC1a channels are the dominant ASIC subtype in mammalian brain (Xiong et al., 2004; Li et al., 2010). The pH for half-maximal activation ($pH_{0.5}$) of ASIC1a is 6.6 in human cortical neurons (Li et al., 2010) and 6.4 in rat Purkinje neurons, and consequently they are robustly activated by the decrease in extracellular pH that occurs during cerebral ischemia. Importantly, homomeric ASIC1a channels can mediate the uptake of $Ca^{2+}$ in addition to $Na^+$ and protons (Gründer and Chen, 2010). Thus, brain ASIC1a can contribute to the intracellular $Ca^{2+}$ overload that occurs during stroke, and the proton permeability of ASIC1a may be at least partly responsible for the precipitous drop in intracellular pH from ~7 to as low as 6.15 during cerebral ischemia (Isaev et al., 2008).

It is now known that cerebral acidosis activates ASIC1a and that this activation is a major contributor to the neuronal damage resulting from stroke (Xiong et al., 2004; Xiong et al., 2007; Wang et al., 2011; Leng et al., 2013). For example, in rodent models of cerebral ischemia, infarct size and neurological deficits are greatly reduced by knockout or pharmacological blockade of ASIC1a (Xiong et al., 2004).

The most potent and selective blocker of ASIC1a described to date is PcTx1 (also known as π-theraphotoxin-Pc1a), a 40-residue peptide isolated from the venom of the Trinidad Chevron tarantula, *Psalmopoeus cambridgei*. PcTx1 inhibits rat ASIC1a (rASIC1a) with an $IC_{50}$ of ~1 nM but it does not inhibit other ASIC homomers or heteromers. In a rat model of transient focal ischemia (middle cerebral artery occlusion; MCAO), intracerebroventricular (i.c.v.) injection of *P. cambridgei* crude venom (that is, without isolating the pure ASIC1a inhibitory peptide) reduced infarct size by 60%. Consistent with this being an effect mediated by ASIC1a, infarct size was similarly reduced by 61% in $ASIC1^{-/-}$ mice (Xiong et al., 2004). Also, infarct size was reduced by ~30% when *P. cambridgei* crude venom was delivered i.c.v. as late as five hours after MCAO (Pignataro et al., 2007).

Whilst PcTx1 appears to be a promising lead molecule for the development of neuroprotective agents for the treatment of stroke, there remains a significant need for compounds that can form the basis of an effective neuroprotective therapy. Given the delay in clinical presentation following stroke, a longer time window for therapeutic intervention would also be advantageous.

It will be clearly understood that, if a prior art publication is referred to herein, this reference does not constitute an admission that the publication forms part of the common general knowledge in the art in Australia or in any other country.

SUMMARY OF INVENTION

The invention is broadly directed to disulfide-rich peptides derived from spider venom and their use as neuroprotective agents, particularly in the treatment of stroke.

In a first aspect, the present invention provides an isolated, synthetic or recombinant disulfide-rich peptide with neuroprotective activity. The peptide comprises, consists of, or consists essentially of, a sequence of Formula (I):

X-L-Y          (I)

wherein X and Y each represent a peptide sequence having an inhibitor cystine knot (ICK) fold and L is a linker, and wherein said peptide is preferably capable of specifically binding to acid sensing ion channel subtype 1a (ASIC1a).

In a second aspect, the present invention provides a functionally active neuroprotective fragment, derivative or analogue of the disulfide-rich peptide provided by the first aspect that is preferably capable of specifically binding to ASIC1a.

In a third aspect, the present invention provides a neuroprotective peptide in which two ICK motifs are joined head-to-tail by a six-residue linker, and wherein said peptide is preferably capable of specifically binding to ASIC1a.

In a fourth aspect, the present invention provides a neuroprotective peptide comprising twelve cysteine residues covalently joined in pairs to form six disulfide bonds, such that the peptide comprises two ICK motifs, and wherein said peptide is preferably capable of specifically binding to ASIC1a.

In a fifth aspect, the present invention provides an isolated, synthetic or recombinant disulfide-rich peptide with neuroprotective activity, wherein the peptide comprises, consists of, or consists essentially of, an amino acid sequence selected from the group consisting of:
- (a) the sequence set forth in any one of SEQ ID NOs:2, 4, 6, 8, 10, 12, 14 or 16;
- (b) a sequence that shares at least 65% (and at least 66% to at least 99% and all integer percentages in between) sequence similarity or sequence identity with the sequence set forth in any one of SEQ ID NOs:2, 4, 6, 8, 10, 12, 14 or 16;
- (c) a sequence that is encoded by the nucleotide sequence set forth in any one of SEQ ID NOs:1, 3, 5, 7, 9, 11 or 13;
- (d) a sequence that is encoded by a nucleotide sequence that shares at least 65% (and at least 66% to at least 99% and all integer percentages in between) sequence similarity or sequence identity with the sequence set forth in any one of SEQ ID NOs: 1, 3, 5, 7, 9, 11 or 13; or
- (e) a sequence that is encoded by a nucleotide sequence that hybridizes under at least medium or high stringency conditions to the sequence set forth in any one of SEQ ID NOs:1, 3, 5, 7, 9, 11 or 13.

In a sixth aspect, the present invention provides an isolated, synthetic or recombinant disulfide-rich peptide derived from spider venom that is capable of specifically binding to ASIC1a.

In a seventh aspect, the present invention provides an isolated, synthetic or recombinant nucleic acid molecule that comprises, consists of, or consists essentially of, a nucleotide sequence encoding the amino acid sequence of the disulfide-rich peptide provided by the first or sixth aspects, the fragment, derivative or analogue provided by the second aspect, or the neuroprotective peptide provided by the third or fourth aspects. In some embodiments, the nucleic acid molecule comprises, consists of, or consists essentially of, a nucleotide sequence selected from the group consisting of:
- (a) the sequence set forth in any one of SEQ ID NOs:1, 3, 5, 7, 9, 11 or 13;
- (b) a sequence that shares at least 65% (and at least 66% to at least 99% and all integer percentages in between) sequence similarity or sequence identity with the sequence set forth in any one of SEQ ID NOs: 1, 3, 5, 7, 9, 11 or 13, or a complement thereof; or
- (c) a sequence that hybridizes under at least medium or high stringency conditions to the sequence set forth in any one of SEQ ID NOs:1, 3, 5, 7, 9, 11 or 11, or a complement thereof.

In an eighth aspect, the present invention provides a genetic construct for expressing the nucleic acid molecule provided by the seventh aspect (for example, for making recombinant peptides in commercial quantities). The genetic construct generally comprises the isolated nucleic acid molecule provided by the seventh aspect operably linked to one or more regulatory sequences in an expression vector.

In a ninth aspect, the present invention provides a host cell transformed with the nucleic acid molecule provided by the seventh aspect or the genetic construct provided by the eighth aspect.

In a tenth aspect, the present invention provides a method of producing the isolated, synthetic or recombinant disulfide-rich peptide provided by the first or sixth aspects, the fragment, derivative or analogue provided by the second aspect, or the neuroprotective peptide provided by the third or fourth aspects, comprising culturing the transformed host cell provided by the ninth aspect and isolating the resultant peptide, fragment, derivative or analogue from said cultured host cell.

In an eleventh aspect, the present invention provides a pharmaceutical composition comprising a therapeutically effective amount of at least one isolated, synthetic or recombinant disulfide-rich peptide provided by the first or sixth aspects, the fragment, derivative or analogue provided by the second aspect, or the neuroprotective peptide provided by the third or fourth aspects.

In a twelfth aspect, the invention provides a method for the treatment of stroke in a subject comprising the step of administering a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect.

In a thirteenth aspect, the invention provides a method for the prevention or treatment of neuronal damage following stroke in a subject comprising the step of administering a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect.

In a fourteenth aspect, the invention provides a method of reducing infarct size following stroke in a subject comprising the step of administering a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect.

In a fifteenth aspect, the invention provides a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect for the treatment of stroke.

In a sixteenth aspect, the invention provides a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect for the prevention or treatment of neuronal damage following stroke in a subject.

In a seventeenth aspect, the invention provides a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect for the reduction of infarct size following stroke in a subject.

In an eighteenth aspect, the invention provides use of at least one isolated, synthetic or recombinant disulfide-rich peptide provided by the first or sixth aspects, the fragment, derivative or analogue provided by the second aspect, or the neuroprotective peptide provided by the third or fourth aspects in the manufacture of a medicament for the treatment of stroke.

In a nineteenth aspect, the invention provides use of at least one isolated, synthetic or recombinant disulfide-rich peptide provided by the first or sixth aspects, the fragment, derivative or analogue provided by the second aspect, or the neuroprotective peptide provided by the third or fourth aspects in the manufacture of a medicament for the prevention or treatment of neuronal damage following stroke in a subject.

In a twentieth aspect, the invention provides use of at least one isolated, synthetic or recombinant disulfide-rich peptide provided by the first or sixth aspects, the fragment, derivative or analogue provided by the second aspect, or the neuroprotective peptide provided by the third or fourth aspects in the manufacture of a medicament for the reduction of infarct size following stroke in a subject.

In a twenty-first aspect, the invention provides use of an isolated, synthetic or recombinant disulfide-rich neuroprotective peptide derived from spider venom for treating stroke.

In a twenty-second aspect, there is provided a method for identifying or designing a peptide, peptidomimetic, or small molecule capable of inhibiting activation of ASIC1a, said method comprising the steps of:
(i) computer modelling the interaction between ASIC1a and at least one disulfide-rich peptide, wherein said disulfide-rich peptide is as defined in any one of the first to sixth aspects;
(ii) using data generated by the computer modelling to identify or design a peptide, peptidomimetic, or small molecule capable of binding to ASIC1a and inhibiting the activation of ASIC1a; and optionally,
(iii) producing the peptide, peptidomimetic, or small molecule of step (ii), and optionally,
(iv) testing the peptide, peptidomimetic, or small molecule of step (iii) for binding to ASIC1a and inhibiting the activation of ASIC1a.

The invention is also more broadly directed to disulfide-rich peptides derived from spider venom and their use as therapeutic or prophylactic agents. Such peptides can be used as therapeutic or prophylactic agents for conditions caused by ASIC1a activity or contributed to by ASIC1a activity in biological pathways.

In a twenty-third aspect, the present invention provides an isolated, synthetic or recombinant disulfide-rich peptide. The peptide comprises, consists of, or consists essentially of, a sequence of Formula (I):

$$X\text{-}L\text{-}Y \qquad (I)$$

wherein X and Y each represent a peptide sequence having an inhibitor cystine knot (ICK) fold and L is a linker, and wherein said peptide is preferably capable of specifically binding to acid sensing ion channel subtype 1a (ASIC1a).

In a twenty-fourth aspect, the present invention provides a functionally active fragment, derivative or analogue of the disulfide-rich peptide provided by the twenty-third aspect that is preferably capable of specifically binding to ASIC1a.

In a twenty-fifth aspect, the present invention provides a peptide in which two ICK motifs are joined head-to-tail by a six-residue linker, and wherein said peptide is preferably capable of specifically binding to ASIC1a.

In a twenty-sixth aspect, the present invention provides a peptide comprising twelve cysteine residues covalently joined in pairs to form six disulfide bonds, such that the peptide comprises two ICK motifs, and wherein said peptide is preferably capable of specifically binding to ASIC1a.

In a twenty-seventh aspect, the present invention provides an isolated, synthetic or recombinant disulfide-rich peptide with therapeutic or prophylactic activity, wherein the peptide comprises, consists of, or consists essentially of, an amino acid sequence selected from the group consisting of:
(a) the sequence set forth in any one of SEQ ID NOs:2, 4, 6, 8, 10, 12, 14 or 16;
(b) a sequence that shares at least 65% (and at least 66% to at least 99% and all integer percentages in between) sequence similarity or sequence identity with the sequence set forth in any one of SEQ ID NOs:2, 4, 6, 8, 10, 12, 14 or 16;
(c) a sequence that is encoded by the nucleotide sequence set forth in any one of SEQ ID NOs:1, 3, 5, 7, 9, 11 or 13;
(d) a sequence that is encoded by a nucleotide sequence that shares at least 65% (and at least 66% to at least 99% and all integer percentages in between) sequence similarity or sequence identity with the sequence set forth in any one of SEQ ID NOs: 1, 3, 5, 7, 9, 11 or 13; or
(e) a sequence that is encoded by a nucleotide sequence that hybridizes under at least medium or high stringency conditions to the sequence set forth in any one of SEQ ID NOs:1, 3, 5, 7, 9, 11 or 13.

In a twenty-eighth aspect, the present invention provides an isolated, synthetic or recombinant disulfide-rich peptide derived from spider venom that is capable of specifically binding to ASIC1a and inhibiting an ASIC1a biological pathway.

In a twenty-ninth aspect, the present invention provides an isolated, synthetic or recombinant nucleic acid molecule that comprises, consists of, or consists essentially of, a nucleotide sequence encoding the amino acid sequence of the disulfide-rich peptide provided by the twenty-third or twenty-eighth aspects, the fragment, derivative or analogue provided by the twenty-fourth aspect, or the peptide provided by the twenty-fifth or twenty-sixth aspects. In some embodiments, the nucleic acid molecule comprises, consists of, or consists essentially of, a nucleotide sequence selected from the group consisting of:

(a) the sequence set forth in any one of SEQ ID NOs:1, 3, 5, 7, 9, 11 or 13;

(b) a sequence that shares at least 65% (and at least 66% to at least 99% and all integer percentages in between) sequence similarity or sequence identity with the sequence set forth in any one of SEQ ID NOs: 1, 3, 5, 7, 9, 11 or 13, or a complement thereof; or (c) a sequence that hybridizes under at least medium or high stringency conditions to the sequence set forth in any one of SEQ ID NOs:1, 3, 5, 7, 9, 11 or 11, or a complement thereof.

In a thirtieth aspect, the present invention provides a genetic construct for expressing the nucleic acid molecule provided by the twenty-ninth aspect (for example, for making recombinant peptides in commercial quantities). The genetic construct generally comprises the isolated nucleic acid molecule provided by the twenty-ninth aspect operably linked to one or more regulatory sequences in an expression vector.

In a thirty-first aspect, the present invention provides a host cell transformed with the nucleic acid molecule provided by the twenty-ninth aspect or the genetic construct provided by the thirtieth aspect.

In a thirty-second aspect, the present invention provides a method of producing the isolated, synthetic or recombinant disulfide-rich peptide provided by the twenty-third or twenty-eighth aspects, the fragment, derivative or analogue provided by the twenty-fourth aspect, or the peptide provided by the twenty-fifth or twenty-sixth aspects, comprising culturing the transformed host cell provided by the thirty-first aspect and isolating the resultant peptide, fragment, derivative or analogue from said cultured host cell.

In a thirty-third aspect, the present invention provides a pharmaceutical composition comprising a therapeutically effective amount of at least one isolated, synthetic or recombinant disulfide-rich peptide provided by the twenty-third or twenty-eighth aspects, the fragment, derivative or analogue provided by the twenty-fourth aspect, or the peptide provided by the twenty-fifth or twenty-sixth aspects.

In a thirty-fourth aspect, the invention provides a method for the prevention or treatment of a condition in a subject caused by ASIC1a activity or contributed to by ASIC1a activity comprising the step of administering a therapeutically effective amount of at least one isolated, synthetic or recombinant disulfide-rich peptide provided by the twenty-third or twenty-eighth aspects, the fragment, derivative or analogue provided by the twenty-fourth aspect, the peptide provided by the twenty-fifth or twenty-sixth aspects or the pharmaceutical composition provided by the thirty-third aspect.

In a thirty-fifth aspect, the invention provides a therapeutically effective amount of at least one isolated, synthetic or recombinant disulfide-rich peptide provided by the twenty-third or twenty-eighth aspects, the fragment, derivative or analogue provided by the twenty-fourth aspect, the peptide provided by the twenty-fifth or twenty-sixth aspects or the pharmaceutical composition provided by the thirty-third aspect for the prevention or treatment of a condition in a subject caused by ASIC1a activity or contributed to by ASIC1a activity.

In a thirty-sixth aspect, the invention provides use of at least one isolated, synthetic or recombinant disulfide-rich peptide provided by the twenty-first or twenty-eighth aspects, the fragment, derivative or analogue provided by the twenty-fourth aspect, or the peptide provided by the twenty-fifth or twenty-sixth aspects in the manufacture of a medicament for the prevention or treatment of a condition in a subject caused by ASIC1a activity or contributed to by ASIC1a activity.

Throughout this specification, unless the context requires otherwise, the words "comprise", "comprises" and "comprising" will be understood to imply the inclusion of a stated integer or group of integers but not the exclusion of any other integer or group of integers.

Any of the features described herein can be combined in any combination with any one or more of the other features described herein within the scope of the invention.

BRIEF DESCRIPTION OF DRAWINGS

FIG. 1. Alignment of the amino acid sequences of members of the π-hexatoxin-Hi1a (Hi1a) superfamily (Hi1a—SEQ ID NO:16; Hi1b—SEQ ID NO:29; Hi1c—SEQ ID NO:30; Hi1d—SEQ ID NO: 31; Hi1e—SEQ ID NO: 32). Cysteine residues are highlighted in white text on a black background. Residues that differ from those found at the corresponding position in Hi1a are highlighted in black text on a grey background. The residue numbers above the alignment refer to Hi1a.

FIG. 7. Effect of Hi1a on the pH-dependence of activation and SSD of rASIC1a (left panel) and hASIC1a (right panel). The activation curves were obtained by applying increasing concentrations of protons every 50 seconds. In the continued presence of protons (pH values below ~7.2 for rASIC1a), ASICs rapidly desensitise and cannot re-open until sufficiently de-protonated (pH values >~7.3 for rASIC1a). SSD profiles were obtained by conditioning the channels for 120 seconds at decreasing pH (mean±SEM; number of experiments=6). The symbols have the same meaning in both panels: ●, no peptide; Δ, 0.5 nM Hi1a; □, 5 nM Hi1a.

BRIEF DESCRIPTION OF SEQUENCES

Figure 2:
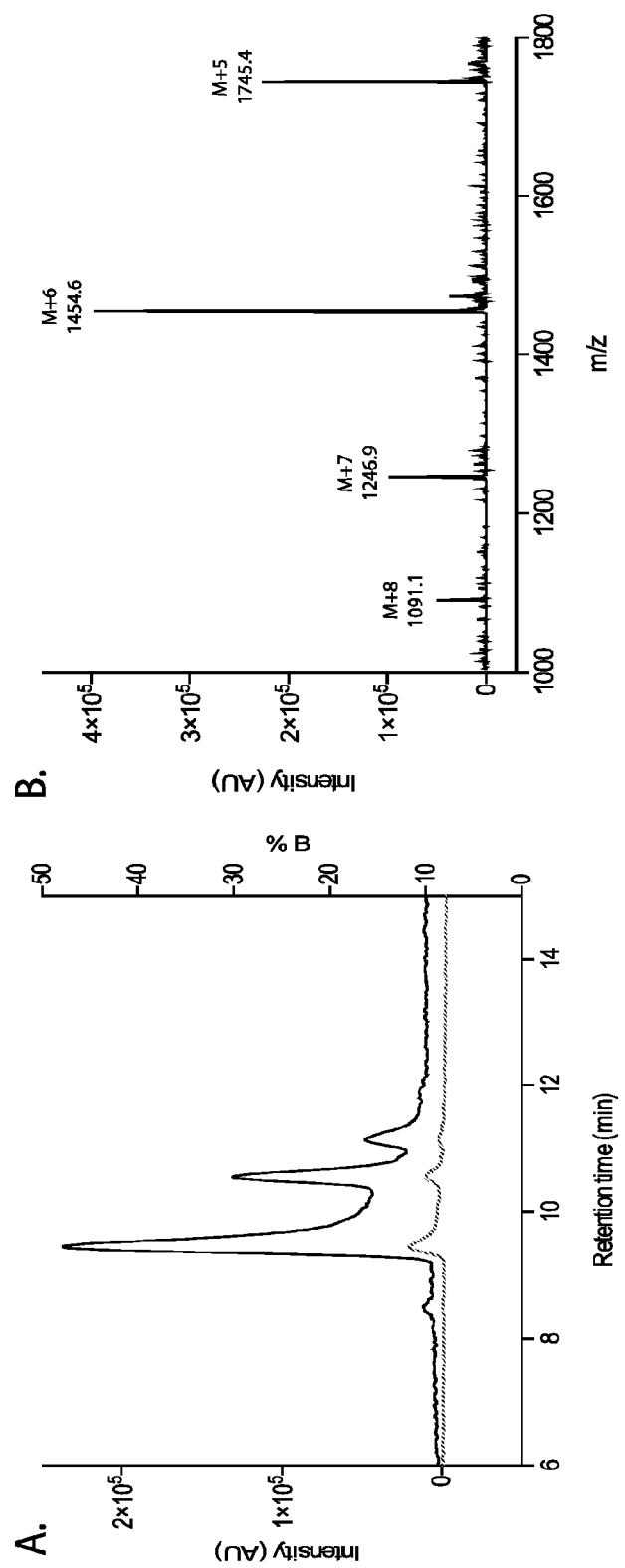
FIG. 2. Characterisation of pure, recombinant Hi1a. (A) Analytical RP-HPLC chromatogram of pure recombinant Hi1a, which elutes as three peaks with the same mass (re-injection of a single peak results again in the appearance of three peaks). This is indicative of conformational isomerism. The top and bottom traces correspond to absorbance at 214 nm and 280 nm, respectively. (B) Electrospray ionisation mass spectrometry (ESI-MS) spectrum of pure recombinant Hi1a. The average mass of 8723 Da indicates that the peptide contains the expected six disulfide bonds.

SEQ ID NO:1=nucleic acid coding sequence of Hi1a-precursor (390 nucleic acids).
SEQ ID NO:2=peptide sequence of Hi1a-precursor (129 amino acids).
SEQ ID NO:3=nucleic acid coding sequence of Hi1b-precursor (390 nucleic acids).
SEQ ID NO:4=peptide sequence of Hi1b-precursor (129 amino acids).
SEQ ID NO:5=nucleic acid coding sequence of Hi1c-precursor (456 nucleic acids).
SEQ ID NO:6=peptide sequence of Hi1c-precursor (151 amino acids).
SEQ ID NO:7=nucleic acid coding sequence of Hi1d-precursor (387 nucleic acids).
SEQ ID NO:8=peptide sequence of Hi1d-precursor (128 amino acids).
SEQ ID NO:9=nucleic acid coding sequence of Hi1e_1-precursor (390 nucleic acids).
SEQ ID NO:10=peptide sequence of Hi1e_1-precursor (129 amino acids).
SEQ ID NO:11=nucleic acid coding sequence of Hi1e_2-precursor (390 nucleic acids).
SEQ ID NO:12=peptide sequence of Hi1e_2-precursor (129 amino acids).
SEQ ID NO:13=nucleic acid coding sequence of Hi1a for expression in *Escherichia coli* (228 nucleic acids).
SEQ ID NO:14=peptide sequence of recombinant Hi1a expressed in *E. coli* (76 amino acids including N-terminal serine which is a vestige of the protease cleavage site).
SEQ ID NO:15=peptide sequence of native mature PcTx1 (40 amino acids).
SEQ ID NO:16=peptide sequence of native mature Hi1a (75 amino acids)
SEQ ID NO:17=peptide sequence of the N-terminal ICK domain of Hi1a (37 amino acids).
SEQ ID NO:18=peptide sequence of the N-terminal ICK domain of Hi1a with a modified C-terminus (VP) and N-terminal serine as vestige of expression system (36 amino acids).
SEQ ID NO:19=peptide sequence of the N-terminal ICK domain of Hi1a with N-terminal serine as vestige of expression system (38 amino acids)
SEQ ID NO:20=peptide sequence of the N-terminal ICK domain of Hi1a with a modified C-terminus (IPG) and N-terminal serine as vestige of expression system (39 amino acids).
SEQ ID NO:21=peptide sequence of the C-terminal ICK domain of Hi1a (40 amino acids)
SEQ ID NO:22=peptide sequence of recombinant Hi1a L8K (76 amino acids)
SEQ ID NO:23=peptide sequence of recombinant Hi1a Y24W (76 amino acids)
SEQ ID NO:24=peptide sequence of recombinant Hi1a H28R (76 amino acids).
SEQ ID NO:25=peptide sequence of recombinant engineered peptide #1 (78 amino acids)
SEQ ID NO:26=peptide sequence of recombinant engineered peptide #2 (78 amino acids)
SEQ ID NO:27=peptide sequence of recombinant engineered peptide #3 (79 amino acids)
SEQ ID NO:28=peptide sequence of recombinant engineered peptide #4, PcTx1:Hi1a_C, the C-terminal ICK domain of Hi1a linked to PcTx1 (81 amino acids).
SEQ ID NO:29=peptide sequence of native mature Hi1b (75 amino acids).
SEQ ID NO:30=peptide sequence of native mature Hi1c (100 amino acids).
SEQ ID NO:31=peptide sequence of native mature Hi1d (77 amino acids).
SEQ ID NO:32=peptide sequence of native mature Hi1e_1 (75 amino acids).
SEQ ID NO:33=peptide sequence of native mature Hi1e_2 (75 amino acids).
SEQ ID NO:34=nucleic acid sequence of the coding sequence used to produce recombinant Hi1a (1416 nucleic acids).
SEQ ID NO:35=amino acid sequence of the full precursor protein for recombinant Hi1a (470 residues).

Description of Embodiments

The present invention is predicated in part on the discovery of a novel disulfide-rich peptide, termed Hi1a, from the venom of the Australian funnel-web spider, *Hadronyche infensa*. Hi1a is an 8.6-kDa peptide containing six disulfide bonds. Hi1a is a double-knot toxin (Bohlen et al., 2010) in which two inhibitor cystine knot (ICK) motifs are joined head-to-tail by a six-residue linker. The ICK motif is a common feature of spider-venom peptides, and it typically results in these peptides having high levels of chemical and thermal stability as well as resistance to proteases. The present inventors have found that Hi1a is the most potent inhibitor of human ASIC1a described to date, and that the peptide is highly selective for ASIC1a over other ASIC subtypes.

By analysing a venom-gland transcriptome from the Australian funnel-web spider, *Hadronyche infensa*, the present inventors identified Hi1a and a number of paralogous peptides.

In a first aspect, the present invention provides an isolated, synthetic or recombinant disulfide-rich peptide with neuroprotective activity. The peptide comprises, consists of, or consists essentially of, a sequence of Formula (I):

X-L-Y     (I)

wherein X and Y each represent a peptide sequence having an inhibitor cystine knot (ICK) fold and L is a linker, and wherein said peptide is preferably capable of specifically binding to ASIC1a.

For the purposes of this invention, "isolated" means material that has been removed from its natural state or otherwise subjected to human manipulation. Isolated material may be substantially or essentially free from components that normally accompany it in its natural state, or may be manipulated so as to be in an artificial state. Isolated material could be material in native or recombinant form. The term "isolated" also encompasses terms such as "purified" and/or "synthetic".

The term "recombinant" as used herein with regards to a peptide or protein means a peptide or protein produced by recombinant techniques.

By "disulfide-rich peptide" in the context of this invention, is meant a peptide having six cysteine residues which are bonded in pairs to form three disulfide bonds. Preferably, the three disulfide bonds form a pseudo-knot known as an inhibitor cystine knot (ICK) motif. Particularly preferred disulfide-rich peptides of the invention comprise twelve cysteine residues covalently joined in pairs to form six disulfide bonds, such that the peptide comprises two ICK motifs.

As used herein, "neuroprotective activity" refers to the effect of reducing or ameliorating damage to neuronal and/or glial cells or tissue such as can occur during stroke. As such, "neuroprotective activity" results in reduced severity of symptoms relating to, for example, sensorimotor function and cognitive ability.

By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In the sequence of Formula (I), X and Y can be different sequences or they can be the same sequence. In preferred embodiments X and Y are different sequences, but both fold to form an ICK motif. Each X and Y is, therefore, preferably a sequence of about 25 to about 50 amino acids, even more preferably, about 30, 31, 32, 33, 34, 35, 36, 37, 38, 39 or 40 amino acids.

In particular embodiments, X has the sequence defined by residues 55 to 87 of SEQ ID NO:2, residues 52 to 84 of SEQ ID NO:6, or residues 1 to 34 of SEQ ID NO:14. Particularly preferred embodiments are those where X has the sequence defined by residues 55 to 87 of SEQ ID NO:2, or residues 1 to 34 of SEQ ID NO:14.

Independently of X, in particular embodiments, Y has the sequence defined by residues 94 to 129 of SEQ ID NO:2, residues 94 to 129 of SEQ ID NO:4, residues 101 to 151 of SEQ ID NO:6, residues 93 to 128 of SEQ ID NO:8, or residues 94 to 129 of SEQ ID NO:10. In a particularly preferred embodiment, Y has the sequence defined by residues 94 to 129 of SEQ ID NO:2.

The linker, L, can be a bond, a non-amino acid-based chemical moiety, a single amino acid, or a peptide sequence. For embodiments where L is a single amino acid, L can be a naturally occurring amino acid or a synthetic, non-naturally occurring amino acid such as a chemical analogue of a corresponding naturally occurring amino acid. In preferred embodiments, L is a peptide sequence of at least 2, 3, 4, 5, 6, 7, 8, 9, 10, 11, 12, 13, 14, 15 or 16 amino acids. The amino acids of the sequence can be the same natural or non-natural amino acid, or each amino acid of the sequence can be independently selected from a naturally occurring amino acid or a synthetic, non-naturally occurring amino acid such as a chemical analogue of a corresponding naturally occurring amino acid. In a particularly preferred embodiment, L is a peptide sequence of six naturally occurring amino acids.

In certain embodiments, L comprises predominantly (that is, more than 50% of the amino acid residues of the linker) naturally occurring hydrophobic amino acids Amino acids having a hydrophobic side chain include tyrosine, valine, isoleucine, leucine, methionine, phenylalanine, tryptophan, alanine and proline.

In particular embodiments, the linker can have the sequence defined by residues 88 to 93 of SEQ ID NO:2, residues 85 to 100 of SEQ ID NO:6, or residues 85 to 92 of SEQ ID NO:8. In a particularly preferred embodiment, the linker has the sequence defined by residues 88 to 93 of SEQ ID NO:2.

The peptides of Formula (I) can comprise any combination of X, Y and L to provide a disulfide-rich peptide capable of specifically binding to ASIC1a. Particularly preferred embodiments comprise a peptide wherein X has the sequence defined by residues 55 to 87 of SEQ ID NO:2 or residues 1 to 34 of SEQ ID NO:14, L has the sequence defined by residues 88 to 93 of SEQ ID NO:2, and Y has the sequence defined by residues 94 to 129 of SEQ ID NO:2, wherein said peptide is capable of specifically binding to ASIC1a.

Preferably, the peptides of Formula (I) have a half-maximal inhibitory concentration ($IC_{50}$) for inhibiting ASIC1a of less than about 10 nM. Even more preferably, the peptides inhibit ASIC1a with an $IC_{50}$ of less than about 1 nM.

In a second aspect, the present invention provides a functionally active neuroprotective fragment, derivative or analogue of the disulfide-rich peptide provided by the first aspect that is preferably capable of specifically binding to ASIC1a.

As used herein, the term "functionally active" means retaining at least 50, 55, 60, 65, 70, 75, 80, 85, 90, 95, 96, 97, 98, 99 or 100% of the neuroprotective activity of the disulfide-rich peptide provided by the first aspect.

The term "fragment" as used herein refers to a sequence that constitutes less than 100%, but at least 20, 30, 40, 50, 55, 60, 65, 70, 75, 80, 85, 90, 95, 96, 97, 98 or 99% of the disulfide-rich peptide.

A "derivative" of the disulfide-rich peptide is a peptide that has been altered, for example by conjugation or complexing with a chemical moiety, by post-translational modification (including, but not limited to, phosphorylation, glycosylation, acetylation, lipidation or pegylation), or by the addition of one or more amino acids (including, for example, the addition of a protein or tag to assist with purification). The incorporation of non-naturally occurring amino acids is also encompassed by "derivative".

As used herein, the term "analogue" refers to a compound that is structurally similar to the disulfide-rich peptide provided by the first aspect, but differs in some aspect.

Preferably, the functionally active neuroprotective fragment, derivative or analogue has a half-maximal inhibitory concentration ($IC_{50}$) for inhibiting ASIC1a of less than about 10 nM. Even more preferably, the functionally active neuroprotective fragment, derivative or analogue inhibits ASIC1a with an $IC_{50}$ of less than about 1 nM.

In a third aspect, the present invention provides a neuroprotective peptide in which two ICK motifs are joined head-to-tail by a six-residue linker, and wherein said peptide is preferably capable of specifically binding to ASIC1a.

The six residues of the linker can be the same naturally occurring or non-naturally occurring amino acid, or each residue of the linker can be independently selected from naturally occurring and non-naturally occurring amino acids. In a particularly preferred embodiment, L is a peptide sequence of six naturally occurring amino acids.

In certain embodiments, the linker comprises predominantly hydrophobic amino acid residues, that is, 4, 5 or 6, naturally occurring hydrophobic amino acids. In a particularly preferred embodiment, the linker has the sequence defined by residues 88 to 93 of SEQ ID NO:2.

The two ICK motifs can be different sequences or they can be the same sequence. In preferred embodiments, the two ICK motifs have different sequences. Each ICK motif is preferably a sequence of about 25 to about 50 amino acids, even more preferably, about 30, 31, 32, 33, 34, 35, 36, 37, 38, 39 or 40 amino acids.

In particular embodiments, the N-terminal ICK motif has the sequence defined by residues 55 to 87 of SEQ ID NO:2, residues 52 to 84 of SEQ ID NO:6, or residues 1 to 34 of SEQ ID NO:14. Particularly preferred embodiments are those where the N-terminal ICK motif has the sequence defined by residues 55 to 87 of SEQ ID NO:2, or residues 1 to 34 of SEQ ID NO:14.

Independently of the N-terminal ICK motif, in particular embodiments, the C-terminal ICK motif has the sequence defined by residues 94 to 129 of SEQ ID NO:2, residues 94 to 129 of SEQ ID NO:4, residues 101 to 151 of SEQ ID NO:6, residues 93 to 128 of SEQ ID NO:8, or residues 94 to 129 of SEQ ID NO:10. In a particularly preferred embodiment, the C-terminal ICK motif has the sequence defined by residues 94 to 129 of SEQ ID NO:2.

The peptides can comprise any combination of ICK motifs with a six-residue linker to provide a neuroprotective peptide capable of specifically binding to ASIC1a. Particularly preferred embodiments comprise a peptide wherein the N-terminal ICK motif has the sequence defined by residues 55 to 87 of SEQ ID NO:2 or residues 1 to 34 of SEQ ID NO:14, the linker has the sequence defined by residues 88 to 93 of SEQ ID NO:2, and the C-terminal ICK motif has the sequence defined by residues 94 to 129 of SEQ ID NO:2, wherein said peptide is capable of specifically binding to ASIC1a.

Preferably, the neuroprotective peptides have a half maximal inhibitory concentration (IC$_{50}$) for inhibiting ASIC1a of less than about 10 nM. Even more preferably, the peptides inhibit ASIC1a with an IC$_{50}$ of less than about 1 nM.

In a fourth aspect, the present invention provides a neuroprotective peptide comprising twelve cysteine residues covalently joined in pairs to form six disulfide bonds, such that the peptide comprises two ICK motifs, and wherein said peptide is preferably capable of specifically binding to ASIC1a. Preferably, the two ICK motifs are joined head-to-tail such that the peptide comprises two concatenated ICK motifs. The two ICK motifs can be joined directly (that is, via a peptide bond) or they can be joined by a linker. The linker can be a non-amino acid-based chemical moiety, a single amino acid, or a peptide sequence. For embodiments where the linker is a single amino acid, the linker can be a naturally occurring or a non-naturally occurring amino acid. For embodiments where the linker is a peptide sequence, the peptide sequence can be at least 2, 3, 4, 5, 6, 7, 8, 9, 10, 11, 12, 13, 14, 15 or 16 amino acids. The amino acids of the linker can be the same natural or non-natural amino acid, or each amino acid of the linker sequence can be independently selected from naturally occurring and non-naturally occurring amino acids. In a particularly preferred embodiment, the linker is a peptide sequence of six naturally occurring amino acids.

In certain embodiments, the linker comprises predominantly (that is, more than 50% of the amino acid residues of the linker) naturally occurring hydrophobic amino acids. In particular embodiments, the linker can have the sequence defined by residues 88 to 93 of SEQ ID NO:2, residues 85 to 100 of SEQ ID NO:6, or residues 85 to 92 of SEQ ID NO:8. In a particularly preferred embodiment, the linker has the sequence defined by residues 88 to 93 of SEQ ID NO:2.

The two ICK motifs can be different sequences or they can be the same sequence. In preferred embodiments, the two ICK motifs have different sequences. Each ICK motif is preferably a sequence of about 25 to about 50 amino acids, even more preferably, about 30, 31, 32, 33, 34, 35, 36, 37, 38, 39 or 40 amino acids.

In particular embodiments, the N-terminal ICK motif has the sequence defined by residues 55 to 87 of SEQ ID NO:2, residues 52 to 84 of SEQ ID NO:6, or residues 1 to 34 of SEQ ID NO:14. Particularly preferred embodiments are those where the N-terminal ICK motif has the sequence defined by residues 55 to 87 of SEQ ID NO:2, or residues 1 to 34 of SEQ ID NO:14.

Independently of the N-terminal ICK motif, in particular embodiments, the C-terminal ICK motif has the sequence defined by residues 94 to 129 of SEQ ID NO:2, residues 94 to 129 of SEQ ID NO:4, residues 101 to 151 of SEQ ID NO:6, residues 93 to 128 of SEQ ID NO:8, or residues 94 to 129 of SEQ ID NO:10. In a particularly preferred embodiment, the C-terminal ICK motif has the sequence defined by residues 94 to 129 of SEQ ID NO:2.

The peptides can comprise any combination of ICK motifs to provide a neuroprotective peptide capable of specifically binding to ASIC1a. Particularly preferred embodiments comprise a peptide wherein the N-terminal ICK motif has the sequence defined by residues 55 to 87 of SEQ ID NO:2 or residues 1 to 34 of SEQ ID NO:14, and the C-terminal ICK motif has the sequence defined by residues 94 to 129 of SEQ ID NO:2, wherein said peptide is capable of specifically binding to ASIC1a.

Preferably, the peptides have a half-maximal inhibitory concentration (IC$_{50}$) for inhibiting ASIC1a of less than about 10 nM. Even more preferably, the peptides inhibit ASIC1a with an IC$_{50}$ of less than about 1 nM.

In a fifth aspect, the present invention provides an isolated, synthetic or recombinant disulfide-rich peptide with neuroprotective activity. The peptide comprises, consists of, or consists essentially of, an amino acid sequence selected from the group consisting of:

(a) the sequence set forth in any one of SEQ ID NOs:2, 4, 6, 8, 10, 12, 14 or 16;

(b) a sequence that shares at least 65% (and at least 66% to at least 99% and all integer percentages in between) sequence similarity or sequence identity with the sequence set forth in any one of SEQ ID NOs:2, 4, 6, 8, 10, 12, 14 or 16;

(c) a sequence that is encoded by the nucleotide sequence set forth in any one of SEQ ID NOs:1, 3, 5, 7, 9, 11 or 13;

(d) a sequence that is encoded by a nucleotide sequence that shares at least 65% (and at least 66% to at least 99% and all integer percentages in between) sequence similarity or sequence identity with the sequence set forth in any one of SEQ ID NOs: 1, 3, 5, 7, 9, 11 or 13; or (e) a sequence that is encoded by a nucleotide sequence that hybridizes under at least medium or high stringency conditions to the sequence set forth in any one of SEQ ID NOs:1, 3, 5, 7, 9, 11 or 13.

The phrase "and all integer percentages in between", as used herein refers to increasing the lower of the two stated values by the integer '1' until the higher of the two stated values is reached. For example, "and at least 66% to at least 99% and all integer percentages in between" refers to at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%.

"Sequence similarity" refers to the percentage number of amino or nucleic acids that are identical or constitute conservative substitutions.

The term "sequence identity" as used herein, refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base or the identical amino acid residue occurs in both sequences to yield the number of matched positions, dividing the number of matched positions by the total number of positions in the window of comparison (i.e., the window size), and multiplying the result by 100 to yield the percentage of sequence identity.

"Hybridizes" is used herein to refer to the pairing of at least partly complementary nucleotide sequences to produce a DNA-DNA, RNA-RNA or DNA-RNA hybrid. Hybrid sequences comprising complementary nucleotide sequences occur through base-pairing.

"Medium or high stringency conditions" refers to the temperature and ionic strength conditions under which sequences will hybridize. The higher the stringency, the higher will be the required level of complementarity between hybridizing nucleotide sequences. Stringency conditions are well-known in the art, with a skilled addressee able to recognize that various factors can be manipulated to optimize the specificity of hybridization (see, for example, Green and Sambrook, 2012).

In a preferred embodiment, the isolated, synthetic or recombinant disulfide-rich peptide comprises SEQ ID NO:16. In a particularly preferred embodiment, the isolated, synthetic or recombinant disulfide-rich peptide consists of SEQ ID NO:14.

In a sixth aspect, the present invention provides an isolated, synthetic or recombinant disulfide-rich peptide derived from spider venom that is capable of specifically binding to ASIC1a. In particular embodiments, the peptide can be derived from the venom of any Australian funnel-web spider from within the genera *Hadronyche, Atrax* or *Illawarra*, or a related mygalomorph spider.

As used herein, "derived" in one sense simply means that the peptide was originally identified in the spider venom. In another sense, "derived" refers to a disulfide-rich peptide that differs from a native peptide by virtue of deletion (truncation) or addition of one or more amino acids to the N-terminal and/or C-terminal end of the native protein, deletion or addition of one or more amino acids at one or more positions within the sequence of the native protein, or substitution of one or more amino acids at one or more sites within the sequence of the native protein.

In a seventh aspect, the present invention provides an isolated, synthetic or recombinant nucleic acid molecule that comprises, consists of, or consists essentially of, a nucleotide sequence encoding the amino acid sequence of the disulfide-rich peptide provided by the first or sixth aspects, the fragment, derivative or analogue provided by the second aspect, or the neuroprotective peptide provided by the third or fourth aspects. In some embodiments, the nucleic acid molecule comprises, consists of, or consists essentially of, a nucleotide sequence selected from the group consisting of:

(a) the sequence set forth in any one of SEQ ID NOs:1, 3, 5, 7, 9, 11 or 13;

(b) a sequence that shares at least 65% (and at least 66% to at least 99% and all integer percentages in between) sequence similarity or sequence identity with the sequence set forth in any one of SEQ ID NOs: 1, 3, 5, 7, 9, 11 or 13, or a complement thereof; or (c) a sequence that hybridizes under at least medium or high stringency conditions to the sequence set forth in any one of SEQ ID NOs:1, 3, 5, 7, 9, 11 or 11, or a complement thereof.

In a preferred embodiment, the isolated nucleic acid molecule comprises SEQ ID NO:13. In a particularly preferred embodiment, the isolated nucleic acid molecule consists of SEQ ID NO:13.

In an eighth aspect, the present invention provides a genetic construct for expressing the nucleic acid molecule provided by the seventh aspect. The genetic construct comprises the isolated nucleic acid molecule provided by the seventh aspect operably linked to one or more regulatory sequences in an expression vector.

Typically, the genetic construct is in the form of, or comprises genetic components of, a plasmid, bacteriophage, a cosmid, a yeast or bacterial artificial chromosome as are well understood in the art (Green and Sambrook, 2012). Genetic constructs may be suitable for maintenance and propagation of the isolated nucleic acid in bacteria or other host cells, for manipulation by recombinant DNA technology and/or expression of the nucleic acid of the second aspect or an encoded protein of the invention.

For the purposes of host cell expression, the genetic construct is an expression construct. Typically, the expression construct comprises the nucleic acid molecule provided by the seventh aspect operably linked to one or more additional sequences in an expression vector. An "expression vector" can be either a self-replicating extra-chromosomal vector such as a plasmid, or a vector that integrates into a host genome (Green and Sambrook, 2012).

The phrase "operably linked" as used herein means placing additional nucleotide sequence(s) relative to the nucleic acid of the second aspect within the genetic construct, wherein the additional nucleotide sequence(s) initiates, regulates or otherwise controls transcription.

Regulatory nucleotide sequences are selected as being appropriate for the host cell used for expression. Numerous types of appropriate expression vectors and suitable regulatory sequences for a variety of host cells are known in the art. The regulatory sequences can include, but are not limited to, promoter sequences (constitutive or inducible), leader or signal sequences, ribosomal binding sites, transcriptional start and termination sequences, translational start and termination sequences, and enhancer or activator sequences.

In some embodiments, the genetic construct further comprises one or more nucleotide sequences such that the disulfide-rich peptide of the invention is expressed as a fusion protein. Preferably the fusion protein comprises a disulfide-rich peptide of the first aspect and one or more moieties. The one or more moieties are known in the art as protein tags. Protein tags are selected based on function and include affinity tags, such as maltose binding protein (MBP), chitin binding protein (CBP), glutathione S-transferase (GST) and poly(His) tag (usually a hexa-histidine tag), and solubilisation tags, such as MBP and GST. The presence of an affinity tag can assist with purification of the fusion protein. For example, a fusion protein comprising a poly (His) tag can be readily purified using immobilized metal ion affinity chromatography (IMAC). The presence of a solubilisation tag can assist with solubility and folding of the expressed protein. Tags such as MBP and GST have dual functionality as affinity tags and solubilisation tags (Sachev and Chirgwin, 2000; Smith, 2000).

In a preferred embodiment of the invention, the genetic construct comprises nucleotide sequences such that the disulfide-rich peptide of the invention is expressed as a fusion protein comprising an affinity tag and a solubilisation tag. In a particularly preferred embodiment, the affinity tag is a poly(His) tag and the solubilisation tag is MBP. The fusion protein preferably further comprises a cleavage site for ease of release of the disulfide-rich peptide from the tags.

In a ninth aspect, the present invention provides a host cell transformed with the nucleic acid molecule provided by the seventh aspect or the genetic construct provided by the eighth aspect.

The host cell can be prokaryotic or eukaryotic. For example, suitable host cells include mammalian cells (such as HeLa, HEK293T or Jurkat), yeast cells (such as *Pichia pastoris*), insect cells (such as Sf9 or *Trichoplusia ni*) utilized with or without a baculovirus expression system, or bacterial cells (such as *E. coli*) (Klint et al., 2013).

In a particularly preferred embodiment, the host cell is *E. coli*.

In an even more preferred embodiment, the host cell is *E. coli* and the disulfide-rich peptide is expressed in the periplasm to take advantage of the disulfide-bond machinery (Dsb system) located in this region of the cell (Klint et al., 2013).

In an alternative embodiment, the disulfide-rich peptides of the invention are produced in a cell-free expression system. Cell-free protein synthesis (also referred to as in vitro translation) has been successfully used for the production of proteins, including disulfide-bonded proteins (Kim and Swartz, 2004; Bundy and Swartz, 2011).

In a tenth aspect, the present invention provides a method of producing the isolated, synthetic or recombinant disulfide-rich peptide provided by the first or sixth aspects, the fragment, derivative or analogue provided by the second aspect, or the neuroprotective peptide provided by the third or fourth aspects, comprising culturing the transformed host cell provided by the ninth aspect and isolating the resultant peptide, fragment, derivative or analogue from said cultured host cell.

The method can comprise further steps, including purification and/or folding. For example, in embodiments where the disulfide-rich peptide is expressed as a fusion protein comprising an affinity tag, as described herein, the method can further comprise purification of the fusion protein using a process suited to the affinity tag. In the case of a poly(His) tag, the purification step can comprise IMAC.

Expression of disulfide-rich peptides does not always result in formation of the correct disulfide bonds, and therefore a non-native fold (three-dimensional structure) can result. A further step in the production of the isolated disulfide-rich peptide of the first aspect can therefore comprise the use of a redox buffer to assist in correct disulfide-bond formation. To avoid interference from impurities, preferably, a redox buffer is utilised after the expressed protein has been purified from the cell culture.

The method can further comprise cleavage of the fusion protein from any affinity and/or solubilisation tags.

In an eleventh aspect, the present invention provides a pharmaceutical composition comprising a therapeutically effective amount of at least one isolated, synthetic or recombinant disulfide-rich peptide provided by the first or sixth aspects, the fragment, derivative or analogue provided by the second aspect, or the neuroprotective peptide provided by the third or fourth aspects.

The phrase "pharmaceutical composition" as used herein encompasses pharmaceutical and veterinary compositions.

Pharmaceutically acceptable carriers, diluents and excipients which can be used in the pharmaceutical compositions of the invention will be known to those of skill in the art. The British Pharmacopoeia (BP) and the United States Pharmacopeia and National Formulary (USP-NF) contain details of suitable carriers, diluents and excipients, as does Sweetman S (Ed.), 'Martindale: The complete drug reference.' London: Pharmaceutical Press, 37th Ed., (2011), and Rowe R C, Sheskey P J, Quinn M E (Ed.), 'Handbook of Pharmaceutical Excipients', 6th Ed., London: Pharmaceutical Press (2009), the contents of which are incorporated herein by cross reference.

The pharmaceutical composition can be formulated for administration by any suitable route. In certain embodiments, the composition is suitable for parenteral administration. The term "parenteral" as used herein includes subcutaneous, intravenous, intramuscular, intra-articular, intra-synovial, intrasternal, intrathecal, intrahepatic, intralesional and intracranial injection or infusion techniques. A particularly preferred mode of administration is intranasal (i.n.).

For i.c.v. or intrathecal administration, the pharmaceutical composition can be formulated in a carrier, such as a diluent, adjuvant, excipient, buffer, stabiliser, isotonicising agent, preservative or anti-oxidant. Preferably, the composition is formulated in a parenterally acceptable aqueous solution which has suitable pH, isotonicity and stability.

For i.n. administration, the peptide, fragment, derivative or analogue can be formulated in a liquid carrier suitable for delivery as a nasal spray. The composition may additionally comprise a delivery enhancer to assist with transport of the peptide, fragment, derivative or analogue across the nasal mucosa. The delivery enhancer can comprise, for example, lipids, polymers, liposomes, emulsions, or nanoparticles.

Similarly, for buccal delivery, the peptide, fragment, derivative or analogue can be formulated in a suitable liquid carrier. The composition preferably further comprises a delivery enhancer to assist with transport of the peptide, fragment, derivative or analogue across the buccal mucosa. The delivery enhancer can comprise, for example, lipids, polymers, liposomes, emulsions, or nanoparticles.

In a twelfth aspect, the invention provides a method for the treatment of stroke in a subject comprising the step of administering a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect.

The subject for treatment can be a human, mammal or animal. Preferably, the subject is a human or other type of mammal.

A "therapeutically effective amount" is the amount effective for treating or lessening the severity of one or more symptoms associated with stroke, including neurological function, neuronal damage, sensorimotor function and cognitive ability.

In preferred embodiments, the therapeutically effective amount of the peptide, fragment, derivative, analogue or pharmaceutical composition is 1-10 ng/kg for i.c.v. delivery and 1-10 µg/kg for intranasal delivery.

Preferably, the step of administering a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect is undertaken as soon as possible after the onset of stroke. The step of administering is preferably undertaken at any time from the onset of the stroke to about 12 hours after the onset of stroke. The step of administering is therefore undertaken no more than 12, 11, 10, 9, 8, 7, 6, 5, 4, 3, 2 or 1 hour(s) after the onset of stroke. Preferably, the step of administering is undertaken no more than 8 hours after the onset of stroke. In an alternative preferred embodiment, the step of administering is undertaken no more than 4 hours after the onset of stroke.

The peptide, fragment, derivative, analogue, or pharmaceutical composition is preferably administered via the i.c.v. or i.n. route.

In a thirteenth aspect, the invention provides a method for the prevention or treatment of neuronal damage following stroke in a subject comprising the step of administering a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect.

In a fourteenth aspect, the invention provides a method for reducing infarct size following stroke in a subject comprising the step of administering a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect.

The subject for treatment can be a human, mammal or animal. Preferably, the subject is a human or other type of mammal.

In preferred embodiments, the therapeutically effective amount of the peptide, fragment, derivative, analogue or pharmaceutical composition is 1-10 ng/kg for i.c.v. delivery and 1-10 µg/kg for intranasal delivery.

The step of administering is preferably undertaken at any time from the onset of the stroke to about 12 hours after the onset of stroke. The step of administering is therefore undertaken no more than 12, 11, 10, 9, 8, 7, 6, 5, 4, 3, 2 or 1 hour(s) after the onset of stroke. Preferably, the step of administering is undertaken no more than 8 hours after the onset of stroke. In an alternative preferred embodiment, the step of administering is undertaken no more than 4 hours after the onset of stroke.

The peptide, fragment, derivative, analogue, or pharmaceutical composition is preferably administered via the i.c.v. or i.n. route.

In a fifteenth aspect, the invention provides a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect for the treatment of stroke.

In a sixteenth aspect, the invention provides a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect for the prevention or treatment of neuronal damage following stroke in a subject.

In a seventeenth aspect, the invention provides use of a therapeutically effective amount of at least one isolated, synthetic or recombinant disulfide-rich peptide provided by the first or sixth aspects, the fragment, derivative or analogue provided by the second aspect, the neuroprotective peptide provided by the third or fourth aspects or the pharmaceutical composition provided by the eleventh aspect for the reduction of infarct size following stroke in a subject.

The subject for treatment can be a human, mammal or animal. Preferably, the subject is a human or other type of mammal.

In preferred embodiments, the therapeutically effective amount of the peptide, fragment, derivative, analogue or pharmaceutical composition is 1-10 ng/kg for i.c.v. delivery and 1-10 µg/kg for intranasal delivery.

The step of administering is preferably undertaken at any time from the onset of the stroke to about 12 hours after the onset of stroke. The step of administering is therefore undertaken no more than 12, 11, 10, 9, 8, 7, 6, 5, 4, 3, 2 or 1 hour(s) after the onset of stroke. Preferably, the step of administering is undertaken no more than 8 hours after the onset of stroke. In an alternative preferred embodiment, the step of administering is undertaken no more than 4 hours after the onset of stroke.

In an eighteenth aspect, the invention provides use of at least one isolated, synthetic or recombinant disulfide-rich peptide provided by the first or sixth aspects, the fragment, derivative or analogue provided by the second aspect, or the neuroprotective peptide provided by the third or fourth aspects in the manufacture of a medicament for the treatment of stroke.

The medicament can be formulated for parenteral administration. Preferably, the medicament is formulated for administration via the i.c.v. or i.n. route.

In preferred embodiments, the medicament is formulated to provide between 1 ng/kg and 2 µg/kg of the peptide, fragment, derivative or analogue. In particularly preferred embodiments, the medicament is formulated to provide 1-2 ng/kg for i.c.v. delivery and 1-2 µg/kg for intranasal delivery.

In a nineteenth aspect, the invention provides use of at least one isolated, synthetic or recombinant disulfide-rich peptide provided by the first or sixth aspects, the fragment, derivative or analogue provided by the second aspect, or the neuroprotective peptide provided by the third or fourth aspects in the manufacture of a medicament for the prevention or treatment of neuronal damage following stroke in a subject.

The medicament can be formulated for parenteral administration. Preferably, the medicament is formulated for administration via the i.c.v. or i.n. route.

In preferred embodiments, the medicament is formulated to provide between 1 ng/kg and 2 µg/kg of the peptide, fragment, derivative or analogue. In particularly preferred embodiments, the medicament is formulated to provide 1-2 ng/kg for i.c.v. delivery and 1-2 µg/kg for intranasal delivery.

In a twentieth aspect, the invention provides use of at least one isolated, synthetic or recombinant disulfide-rich peptide provided by the first or sixth aspects, the fragment, derivative or analogue provided by the second aspect, or the neuroprotective peptide provided by the third or fourth aspects in the manufacture of a medicament for the reduction of infarct size following stroke in a subject.

The medicament can be formulated for parenteral administration. Preferably, the medicament is formulated for administration via the i.c.v. or i.n. route.

In preferred embodiments, the medicament is formulated to provide between 1 ng/kg and 2 µg/kg of the peptide, fragment, derivative or analogue. In particularly preferred embodiments, the medicament is formulated to provide 1-2 ng/kg for i.c.v. delivery and 1-2 µg/kg for intranasal delivery.

In a twenty-first aspect, the invention provides use of an isolated, synthetic or recombinant disulfide-rich neuroprotective peptide derived from spider venom for treating stroke. In particular embodiments, the peptide can be derived from the venom of any Australian funnel-web spider from within the genera *Hadronyche, Atrax* and *Illawarra*, or a related mygalomorph spider.

In a twenty-second aspect, there is provided a method for identifying or designing a peptide, peptidomimetic, or small molecule capable of inhibiting activation of ASIC1a, said method comprising the steps of:
  (i) computer modelling the interaction between ASIC1a and at least one disulfide-rich peptide, wherein said disulfide-rich peptide is as defined in any one of the first to sixth aspects;
  (ii) using data generated by the computer modelling to identify or design a peptide, peptidomimetic, or small molecule capable of binding to ASIC1a and inhibiting the activation of ASIC1a; and optionally,
  (iii) producing the peptide, peptidomimetic, or small molecule of step (ii), and optionally,
  (iv) testing the peptide, peptidomimetic, or small molecule of step (iii) for binding to ASIC1a and inhibiting the activation of ASIC1a.

Preferably, the peptide, peptidomimetic, or small molecule is capable of specifically binding to ASIC1a. Even more preferably, the peptide, peptidomimetic, or small molecule has an $IC_{50}$ for inhibiting ASIC1a of less than about 10 nM. In particularly preferred embodiments, the peptide, peptidomimetic, or small molecule inhibits ASIC1a with an $IC_{50}$ of less than about 1 nM.

In further preferred embodiments, the peptide, peptidomimetic, or small molecule is a peptide falling within the scope of the fifth aspect.

Other particularly preferred aspects of the invention are defined below and can have one or more features as described in respect of the first to twenty-second aspects, or as described elsewhere in this specification.

In a twenty-third aspect, the present invention provides an isolated, synthetic or recombinant disulfide-rich peptide. The peptide comprises, consists of, or consists essentially of, a sequence of Formula (I):

X-L-Y     (I)

wherein X and Y each represent a peptide sequence having an inhibitor cystine knot (ICK) fold and L is a linker, and wherein said peptide is preferably capable of specifically binding to acid sensing ion channel subtype 1a (ASIC1a).

In a twenty-fourth aspect, the present invention provides a functionally active fragment, derivative or analogue of the disulfide-rich peptide provided by the twenty-third aspect that is preferably capable of specifically binding to ASIC1a.

In a twenty-fifth aspect, the present invention provides a peptide in which two ICK motifs are joined head-to-tail by a six-residue linker, and wherein said peptide is preferably capable of specifically binding to ASIC1a.

In a twenty-sixth aspect, the present invention provides a peptide comprising twelve cysteine residues covalently joined in pairs to form six disulfide bonds, such that the peptide comprises two ICK motifs, and wherein said peptide is preferably capable of specifically binding to ASIC1a.

In a twenty-seventh aspect, the present invention provides an isolated, synthetic or recombinant disulfide-rich peptide with therapeutic or prophylactic activity, wherein the peptide comprises, consists of, or consists essentially of, an amino acid sequence selected from the group consisting of:
  (a) the sequence set forth in any one of SEQ ID NOs:2, 4, 6, 8, 10, 12, 14 or 16;
  (b) a sequence that shares at least 65% (and at least 66% to at least 99% and all integer percentages in between) sequence similarity or sequence identity with the sequence set forth in any one of SEQ ID NOs:2, 4, 6, 8, 10, 12, 14 or 16;
  (c) a sequence that is encoded by the nucleotide sequence set forth in any one of SEQ ID NOs:1, 3, 5, 7, 9, 11 or 13;
  (d) a sequence that is encoded by a nucleotide sequence that shares at least 65% (and at least 66% to at least 99% and all integer percentages in between) sequence similarity or sequence identity with the sequence set forth in any one of SEQ ID NOs: 1, 3, 5, 7, 9, 11 or 13; or
  (e) a sequence that is encoded by a nucleotide sequence that hybridizes under at least medium or high stringency conditions to the sequence set forth in any one of SEQ ID NOs:1, 3, 5, 7, 9, 11 or 13.

In a twenty-eighth aspect, the present invention provides an isolated, synthetic or recombinant disulfide-rich peptide derived from spider venom that is capable of specifically binding to ASIC1a and inhibiting an ASIC1a biological pathway.

In a twenty-ninth aspect, the present invention provides an isolated, synthetic or recombinant nucleic acid molecule that comprises, consists of, or consists essentially of, a nucleotide sequence encoding the amino acid sequence of the disulfide-rich peptide provided by the twenty-third or twenty-eighth aspects, the fragment, derivative or analogue provided by the twenty-fourth aspect, or the peptide provided by the twenty-fifth or twenty-sixth aspects. In some embodiments, the nucleic acid molecule comprises, consists of, or consists essentially of, a nucleotide sequence selected from the group consisting of:
  (a) the sequence set forth in any one of SEQ ID NOs:1, 3, 5, 7, 9, 11 or 13;
  (b) a sequence that shares at least 65% (and at least 66% to at least 99% and all integer percentages in between) sequence similarity or sequence identity with the sequence set forth in any one of SEQ ID NOs: 1, 3, 5, 7, 9, 11 or 13, or a complement thereof; or
  (c) a sequence that hybridizes under at least medium or high stringency conditions to the sequence set forth in any one of SEQ ID NOs:1, 3, 5, 7, 9, 11 or 11, or a complement thereof.

In a thirtieth aspect, the present invention provides a genetic construct for expressing the nucleic acid molecule provided by the twenty-ninth aspect (for example, for making recombinant peptides in commercial quantities). The genetic construct generally comprises the isolated nucleic acid molecule provided by the twenty-ninth aspect operably linked to one or more regulatory sequences in an expression vector.

In a thirty-first aspect, the present invention provides a host cell transformed with the nucleic acid molecule provided by the twenty-ninth aspect or the genetic construct provided by the thirtieth aspect.

In a thirty-second aspect, the present invention provides a method of producing the isolated, synthetic or recombinant disulfide-rich peptide provided by the twenty-third or twenty-eighth aspects, the fragment, derivative or analogue provided by the twenty-fourth aspect, or the peptide provided by the twenty-fifth or twenty-sixth aspects, comprising culturing the transformed host cell provided by the thirty-first aspect and isolating the resultant peptide, fragment, derivative or analogue from said cultured host cell.

In a thirty-third aspect, the present invention provides a pharmaceutical composition comprising a therapeutically effective amount of at least one isolated, synthetic or recombinant disulfide-rich peptide provided by the twenty-third or twenty-eighth aspects, the fragment, derivative or analogue provided by the twenty-fourth aspect, or the peptide provided by the twenty-fifth or twenty-sixth aspects.

In a thirty-fourth aspect, the invention provides a method for the prevention or treatment of a condition in a subject caused by ASIC1a activity or contributed to by ASIC1a activity comprising the step of administering a therapeutically effective amount of at least one isolated, synthetic or recombinant disulfide-rich peptide provided by the twenty-third or twenty-eighth aspects, the fragment, derivative or analogue provided by the twenty-fourth aspect, the peptide provided by the twenty-fifth or twenty-sixth aspects or the pharmaceutical composition provided by the thirty-third aspect.

In a thirty-fifth aspect, the invention provides a therapeutically effective amount of at least one isolated, synthetic or recombinant disulfide-rich peptide provided by the twenty-third or twenty-eighth aspects, the fragment, derivative or analogue provided by the twenty-fourth aspect, the peptide provided by the twenty-fifth or twenty-sixth aspects or the pharmaceutical composition provided by the thirty-third aspect for the prevention or treatment of a condition in a subject caused by ASIC1a activity or contributed to by ASIC1a activity.

In a thirty-sixth aspect, the invention provides use of at least one isolated, synthetic or recombinant disulfide-rich peptide provided by the twenty-first or twenty-eighth aspects, the fragment, derivative or analogue provided by the twenty-fourth aspect, or the peptide provided by the twenty-fifth or twenty-sixth aspects in the manufacture of a medicament for the prevention or treatment of a condition in a subject caused by ASIC1a activity or contributed to by ASIC1a activity.

Conditions in subjects caused by ASIC1a activity or contributed to by ASIC1a activity can be gleaned from other parts of this specification as well as from references cited in this specification, the entire contents of which are incorporated herein by cross-reference.

It will be appreciated that the following examples have been provided for the purpose of illustrating preferred embodiments of the present invention. Therefore, it would be understood that the present invention should not be considered to be limited solely to the features as described in the examples.

EXAMPLES

Example 1—Transcriptomic Analysis

Three specimens of the Australian funnel-web spider *Hadronyche infensa* were milked to exhaust their venom supply and then three days later the specimens were anesthetised. The paired venom glands were dissected from each specimen and immediately placed in TRIzol® reagent (Life Technologies). Total RNA was extracted by standard methods, and mRNA enrichment from total RNA was performed using the Oligotex direct mRNA mini kit (Qiagen). RNA quality and concentration was measured using a Bioanalyzer 2100 pico chip (Agilent Technologies).

100 ng of mRNA was used to construct a cDNA library using the standard cDNA rapid library preparation and emulsion PCR method (Roche). Sequencing was performed at the Brisbane node of the Australian Genome Research Facility using a Roche GS-FLX sequencer. The Raw Standard Flowgram File (.SFF) was processed and low-quality sequences discarded using a Phred score cut-off of 25 (Pandey et al., 2010). De novo assembly was undertaken using MIRA software (Chevreux et al., 2004) using the following parameters: -GE:not=4--project=Hinfensa --job=denovo,est,accurate,454 454_SETTINGS -CL:qc=no -AS:mrpc=1-AL:mrs=99,egp=1. The assembled data set was visualised using TABLET (Milne et al., 2010) or Geneious software (Drummond et al., 2011). Consensus sequences were submitted to the Blast2GO software suite acquire BLAST and functional annotations (Conesa et al., 2005). Signal sequences were determined using the SignalP algorithm (Bendtsen et al., 2004). Putative propeptide cleavage sites were predicted using the results of a sequence logo analysis of all known spider-toxin precursors reported on the ArachnoServer database (Herzig et al., 2011). After determining all processing signals, toxins were classified into superfamilies based on their signal sequence and cysteine framework. One superfamily comprised a peptide designated Hi1a and a number of orthologs with a high level of sequence identity with Hi1a. A sequence alignment of the five members of the Hi1a family is shown in FIG. 1.

Example 2—Recombinant Protein Expression

Synthetic genes encoding Hi1a, or derivatives thereof, with codons optimised for expression in *E. coli*, were produced and subcloned into a pLiCc vector by GeneArt (as described in Klint et al. 2013). The pLiCc plasmid contains a LacI promoter that is inducible by isopropyl β-D-1-thiogalactopyranoside (IPTG) and a β-lactamase gene for selection of transformants using ampicillin Hi1a was encoded as a MalE-His$_6$-MBP-Hi1a fusion protein. MalE is a signal sequence that targets the expressed fusion protein to the *E. coli* periplasm where the Dsb enzymes that catalyse disulfide-bond formation are located. The His$_6$ tag enables facile purification of the fusion protein by IMAC chromatography, while the MBP tag aids protein solubility. A tobacco etch virus (TEV) protease recognition site was introduced between the MBP and Hi1a-coding regions so that Hi1a could be released from the fusion protein using TEV protease. Cleavage of Hi1a from the fusion protein results in an additional serine residue at the N-terminus of Hi1a, which is a vestige of the TEV protease cleavage site.

*E. coli* BL21 (XDE3) cells were transformed with pLiCc vector containing a codon-optimised Hi1a gene. Cultures of this *E. coli* strain were grown in Luria-Bertani (LB) medium at 30° C., then Hi1a expression was induced with 0.5 mM isopropyl β-D-1-thiogalactopyranoside (IPTG) at $OD_{600}$=0.8-1.3. Cells were then grown overnight at 16° C., harvested by centrifugation, and then lysed under constant pressure (27 kpsi) using a cell disrupter (TS Series Cell Disrupter, Constant Systems Ltd, Daventry, UK). The lysate was centrifuged at 4° C. using a Beckman Avanti J-26 centrifuge and then the supernatant was passed over a Ni-NTA Superflow resin (Qiagen) in order to capture the $His_6$-MBP-Hi1a fusion protein. The resin was then washed with 10 mM imidazole to remove non-specific binders, then the $His_6$-MBP-Hi1a protein was eluted with 400 mM imidazole. A 30-kDa cut-off centrifugal filter (Millipore) was used to remove imidazole and concentrate the fusion protein into ~5 mL of TN buffer (20 mM Tris-HCl, 200 mM NaCl, pH 7.8). To this solution, 5 mL of redox buffer (0.6 mM reduced and 0.4 mM oxidised glutathione) was added. Finally, 100 μg of TEV protease was added and the mixture was incubated at room temperature overnight to release Hi1a from the $His_6$-MBP fusion protein. The final yield of recombinant Hi1a is typically about 100-200 micrograms per litre of bacterial culture. The recombinant Hi1a contain a non-native serine residue at the N-terminus that was added to facilitate TEV cleavage.

1% trifluoroacetic acid (TFA) was added to solutions containing the products of the $His_6$-MBP-Hi1a cleavage reaction. Hi1a was then isolated from salts, TEV protease, $His_6$-MBP, and uncleaved $His_6$-MBP-Hi1a using a Shimadzu Prominence high-performance liquid chromatography (HPLC) system. Separation was performed on a semi-preparative $C_4$ reversed-phase (RP) HPLC column (Phenomenex, C4, 250×10 mm, particle size 10 μm), using a flow rate of 5 mL/min and an elution gradient of 10-50% solvent B (90% acetonitrile, 10% $H_2O$, 0.043% TFA) over 30 min.

The molecular masses of purified peptides were determined using an API-2000 ESI-QdQ triple quadrupole mass spectrometer (Applied Biosystems, Calif., USA).

A RP-HPLC chromatogram of pure recombinant Hi1a is shown in FIG. 2A. Hi1a elutes as three peaks which have the same mass. Re-injection of any of these single peaks results in the re-appearance of three peaks, indicating that the peptide undergoes conformational isomerism. The ESI-MS trace for pure recombinant Hi1a is shown in FIG. 2B. The average mass of 8723 Da indicates that the peptide contains six disulfide bonds.

Example 3—Peptide Activity

The ability of the peptides of the invention to modulate ASIC currents was assessed using two-electrode voltage clamp (TEVC) electrophysiology experiments performed on *Xenopus laevis* oocytes expressing homomeric ASIC channels. Xenopus oocytes are widely used as an expression system for functional characterisation of ion channel modulators. TEVC allows measurement of whole-cell ion channel currents while controlling the membrane potential.

Oocytes were harvested from anaesthetised female *X. laevis* then defolliculated by treatment with collagenase (Sigma, type I). Oocytes were injected with in vitro transcribed ASIC cRNA (capped RNA). Oocytes were kept at 17-18° C. in ND96 solution containing 96 mM NaCl, 2 mM KCl, 1.8 mM $CaCl_2$, 2 mM $MgCl_2$, 5 mM HEPES, 5 mM pyruvic acid, 50 μg/ml gentamicin (pH 7.4), and fetal horse serum (2.5%), and experiments were performed at room temperature (21-22° C.) 1-3 days after cRNA injection. Oocytes were clamped at −60 mV (Warner OC-725C oocyte clamp; Warner Instruments, CT, USA) using two standard glass microelectrodes of 0.5-2 MΩ resistance when filled with 3 M KCl. Data acquisition and analysis were performed using pCLAMP software, Version 10 (Axon Instruments, CA, USA). Currents were elicited by a drop in pH from 7.45 to 6.0 using a microperfusion system to allow rapid solution exchange. All experiments were performed using ND96 solution spiked with 0.1% BSA in order to minimise adsorption of peptides to plastic tubing.

Figure 3:
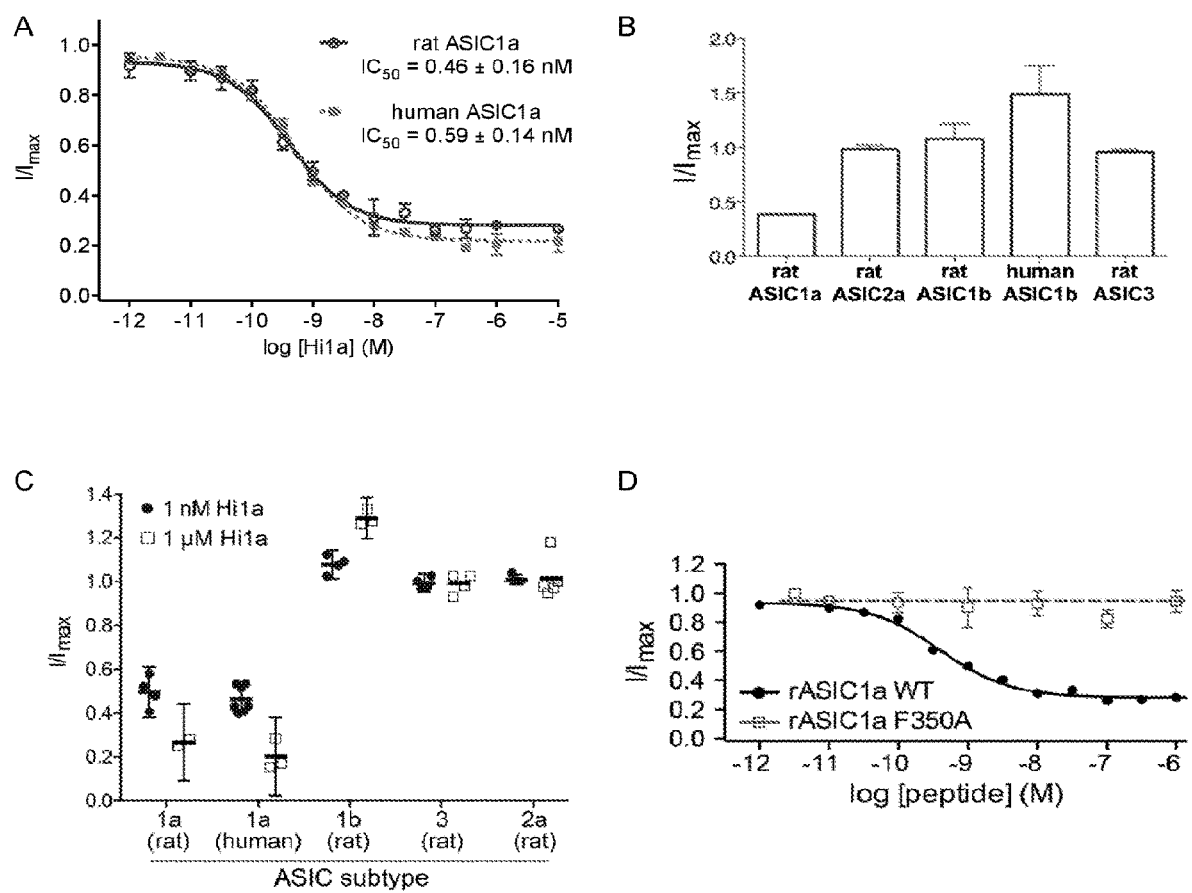
FIG. 3. Functional characterisation of recombinant Hi1a. (A) Concentration response curves for inhibition of rASIC1a and hASIC1a by Hi1a (Note: data are mean±SEM; number of experiments=8). $I/I_{max}$: test current/control current. (B) Effect of 30 nM Hi1a at pH 7.45 on various ASIC subtypes and point mutants (Note: data are mean±SEM; number of experiments=5). (C) Effect of 1 nM and 1 µM Hi1a at pH 7.45 on various ASIC subtypes expressed in Xenopus oocytes. Individual data points are shown as well as mean±SEM; number of experiments=5. (D) Concentration dependent effects of Hi1a on wild-type rASIC1a and an F350A mutant rASIC1a channel expressed in Xenopus oocytes.

Concentration effect curves for inhibition of rASIC1a and hASIC1a by Hi1a are shown in FIG. 3A (mean±SEM; number of experiments=8; $I/I_{max}$: test current/control current). Fitting of the Hill equation to the concentration-effect data revealed that Hi1a inhibits rat ASIC1a with a half-maximal inhibitory concentration ($IC_{50}$) of 0.46±0.16 nM and human ASIC1a with an $IC_{50}$ of 0.59±0.14 nM. The curves also indicate that inhibition of ASIC1a by Hi1a is incomplete, with ~30% of rASIC1a and ~20% of hASIC1a currents remaining at saturating concentrations of the Hi1a peptide.

The effect of 30 nM Hi1a at pH 7.45 on various ASIC subtypes is shown in FIG. 3B (mean±SEM; number of experiments =5). At this dose, Hi1a had a minimal effect on rASIC1b, rASIC2a and rASIC3, indicating that Hi1a has at least 50-fold selectivity for ASIC1a over these other subtypes. The effect of 1 nM and 1 μM Hi1a at pH 7.45 on various ASIC subtypes is shown in FIG. 3C (mean±SEM; number of experiments =5). At 1 μM, Hi1a had no effect on homomeric rASIC2a or rASIC3, and it mildly potentiated rASIC1b, indicating >2000-fold higher potency at ASIC1a over these other subtypes.

FIG. 3D shows that Hi1a had no activity on an F350A mutant of rASIC1a. The crystal structure of chicken ASIC1 (Jasti et al., 2007) reveals that residue F350 is located on an a-helix in an acidic pocket that is important for proton gating of the channel Mutation of this Phe residue to Ala abolishes the ability of another spider-venom peptide, PcTx1, to inhibit ASIC1a (Sherwood et al., 2009). Thus, the binding sites for PcTx1 and Hi1a on ASIC1a at least partly overlap.

Figure 4:
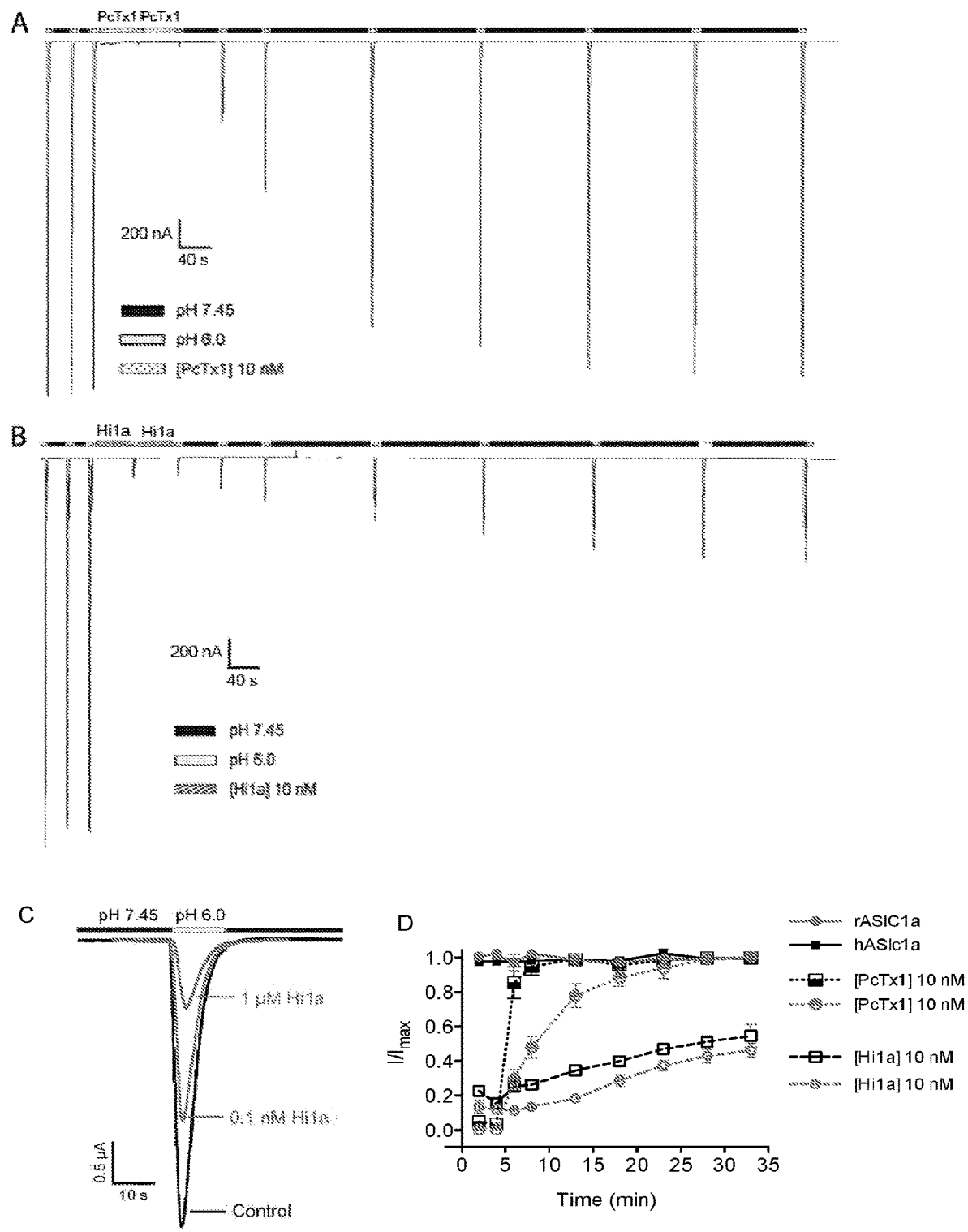
FIG. 4. Representative recordings of experiments performed on Xenopus oocytes expressing rASIC1a channels. Whole-cell currents were elicited by a drop in extracellular pH from 7.45 to 6.0, every 60 seconds (and every 5 minutes during peptide washout). Oocytes expressing channels were exposed to (A) PcTx1 and (B) Hi1a (at a constant concentration of 10 nM) at pH 7.45 for 120 seconds twice. (C) Representative current traces in the absence (control) and presence of Hi1a (0.1 nM and 1 µM) showing incomplete current inhibition with 1 µM Hi1a (saturating concentration). (D) Graph of ASIC1a current versus time after peptide washout showing the rapid, fully reversible inhibition of ASIC1a by PcTx1 compared to the very slow reversibility of the inhibitory action of Hi1a (~40% recovery of current amplitude after 30 minutes of washout) (mean±SEM; number of experiments=5).

The inhibition of ASIC1a by PcTx1 is rapidly reversible upon washout of the peptide (fully reversible within ~15 minutes). In contrast, the inhibitory effect of Hi1a at the same concentration (10 nM) is very slowly reversible with only ~40% recovery of current amplitude recovered after 30 minutes of washout as shown in FIG. 4.

Example 4—Mechanism of Action of Hi1a on ASIC1a

Figure 5:
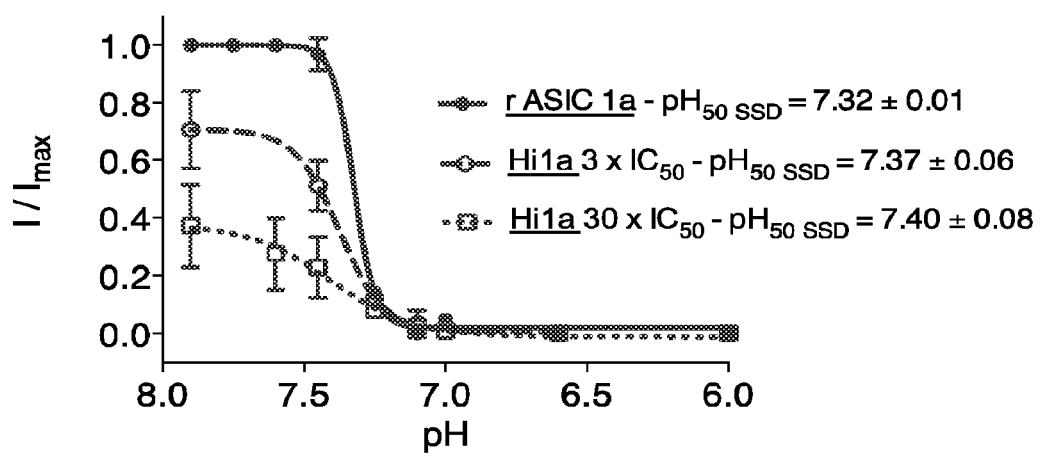
FIG. 5. Modulatory effect of Hi1a on ASIC1a steady-state desensitisation. Effect of increasing concentrations of Hi1a on the steady-state desensitisation (SSD) of rASIC1a. Control currents were taken using a pH drop from 7.45 to pH 5, then the SSD curve was obtained by conditioning the channel for 120 seconds at pH 7.9, 7.75, 7.6, 7.45, 7.3, 7.2, 7.0 in the absence and presence of peptide (mean±SEM; number of experiments=5).

The mechanism of action of Hi1a on ASIC1a was examined using TEVC electrophysiology. PcTx1 mimics the effect of protonation of ASIC1a, leading to chronic desensitisation at a physiological pH of 7.4 (indicated by a parallel shift in the steady-state desensitisation (SSD) curve to more alkaline values with no decrease in the maximum current). The effect of two concentrations of Hi1a on the SSD curves of rat and human ASIC1a were assessed and it was determined that Hi1a does not cause a concentration-dependent parallel shift in the SSD curve to more alkaline values. Instead, Hi1a causes a pH-independent decrease in the maximum current (FIGS. 5 and 7), indicating that Hi1a inhibits ASIC1a with a mode of action that differs from that of PcTx1. Unlike PcTx1, Hi1a appears to inhibit activation rather than stabilizing the desensitised state.

Figure 6:
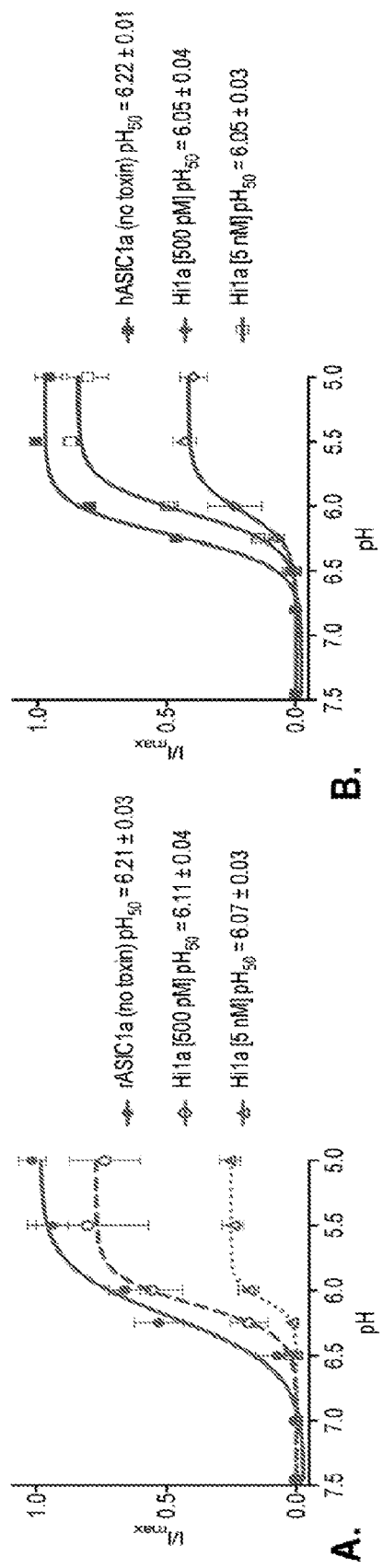
FIG. 6. Modulatory effect of Hi1a on ASIC1a activation. Effect of increasing concentrations of Hi1a on the acid-evoked activation of (A) rASIC1a and (B) hASIC1a. The activation curves were obtained by conditioning the channel at pH 7.45 for 60 seconds in between increasing acidic stimuli from pH 7 to 5, in the absence and presence of recombinant peptide (mean±SEM; number of experiments=5).
Figure 7:
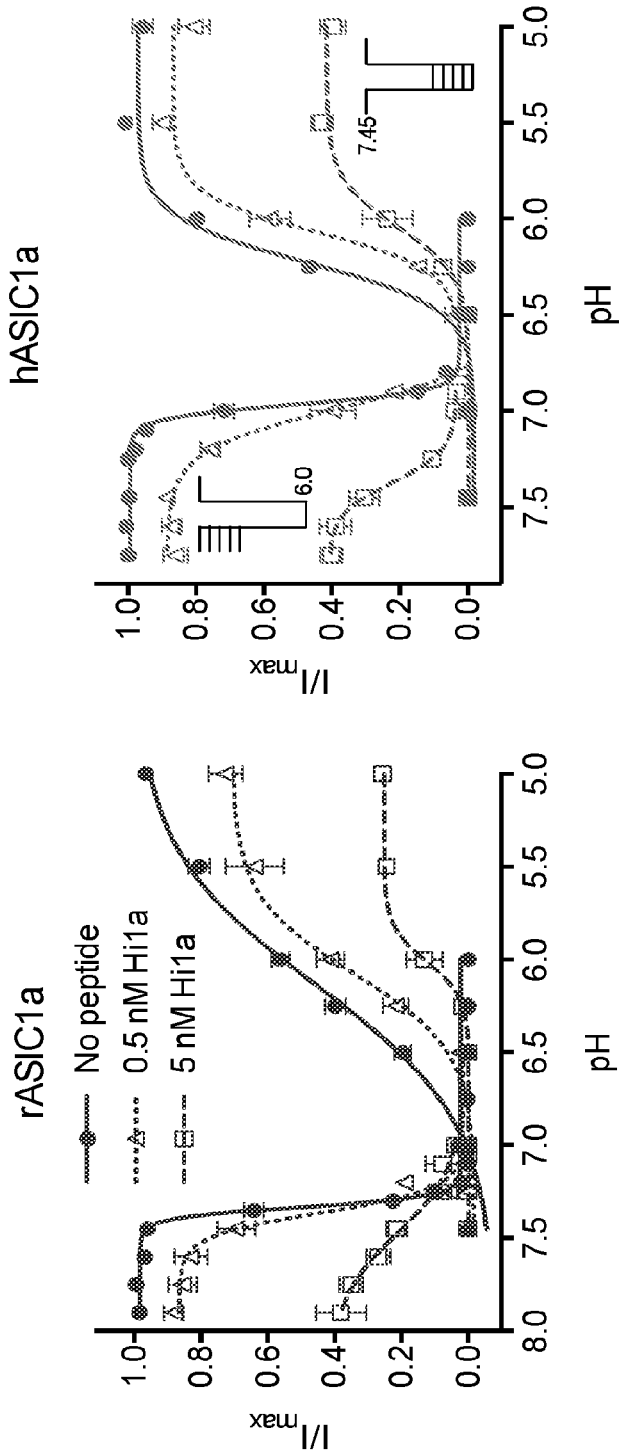

The ability of Hi1a to affect the pH-dependence of ASIC1a activation was also assessed (FIGS. 6 and 7). In the presence of Hi1a (applied at pH 7.45), the $pH_{50}$ of activation is shifted to slightly lower values in a concentration-dependent manner, for both rASIC1a and hASIC1a. This suggests that Hi1a inhibits ASIC1a by increasing the activation threshold, therefore preventing activation. This effect on activation is the opposite of that observed with PcTx1. When applied at pH 7.9, PcTx1 shifts the activation curve for ASIC1a to more alkaline values, that is, it makes the channel more sensitive to protons (Chen et al., 2005). The present results indicate that Hi1a makes ASIC1a less sensitive to protons in an insurmountable way (that is, the antagonism is not competitive).

Example 5—Structure-Activity Relationships

The structure of Hi1a was determined using heteronuclear NMR spectroscopy. NMR data were acquired at 298 K on a Bruker Avance II+ 900 MHz spectrometer equipped with a cryogenically cooled triple-resonance probe using a 300 μM sample of $^{13}C/^{15}N$-labelled Hi1a dissolved in 20 mM 2-(N-morpholino) ethanesulfonic acid (MES) buffer, 0.02% NaN3 and 5% $D_2O$. Sequence-specific resonance assignments were obtained using a combination of 2D $^1H$-$^{15}N$-HSQC, 2D $^1H$-$^{13}C$-HSQC, 3D HNCACB, 3D CBCA(CO)NH, 3D HNCO, and 3D HBHA(CO)NH spectra. Sidechain resonance assignments were made using a 4D HCC(CO)NH-TOCSY spectrum which has the advantage of providing direct sidechain $^{13}C$-$^1H$ connectivities. All 3D and 4D spectra were acquired using non-uniform sampling (NUS) and processed using maximum entropy reconstruction. Chemical shift assignments for Hi1a have been deposited in BioMagResBank (BMRB) under accession code 25848.

Inter-proton distance restraints for structure calculations were derived from $^{13}C$-aliphatic, $^{13}C$-aromatic and $^{15}N$-edited NOESY-HSQC spectra acquired using uniform sampling with a mixing time of 200 ms. Resonance assignments, as well as peak picking and integration of NOESY spectra, were achieved manually using SPARKY, then peaklists were assigned and an ensemble of structures calculated automatically using the torsion angle dynamics package CYANA 3.0. The chemical shift tolerances used for auto-assignment in CYANA were 0.025 ppm and 0.030 ppm for the direct and indirect $^1H$ dimensions, respectively, and 0.30 ppm for the heteronucleus ($^{13}C/^{15}N$). Backbone dihedral-angle restraints derived from TALOS chemical shift analysis were also incorporated into structure calculations with the restraint range set to twice the estimated standard deviation. Disulfide-bond connectivities were determined unambiguously in the first round of structure calculations and corresponding disulfide-bond restraints were applied in subsequent calculations as described previously. CYANA was used to calculate 200 structures from random starting conformations, then the 20 conformers with highest stereochemical quality as judged by MolProbity were selected to represent the solution structure of Hi1a.

Figure 8:
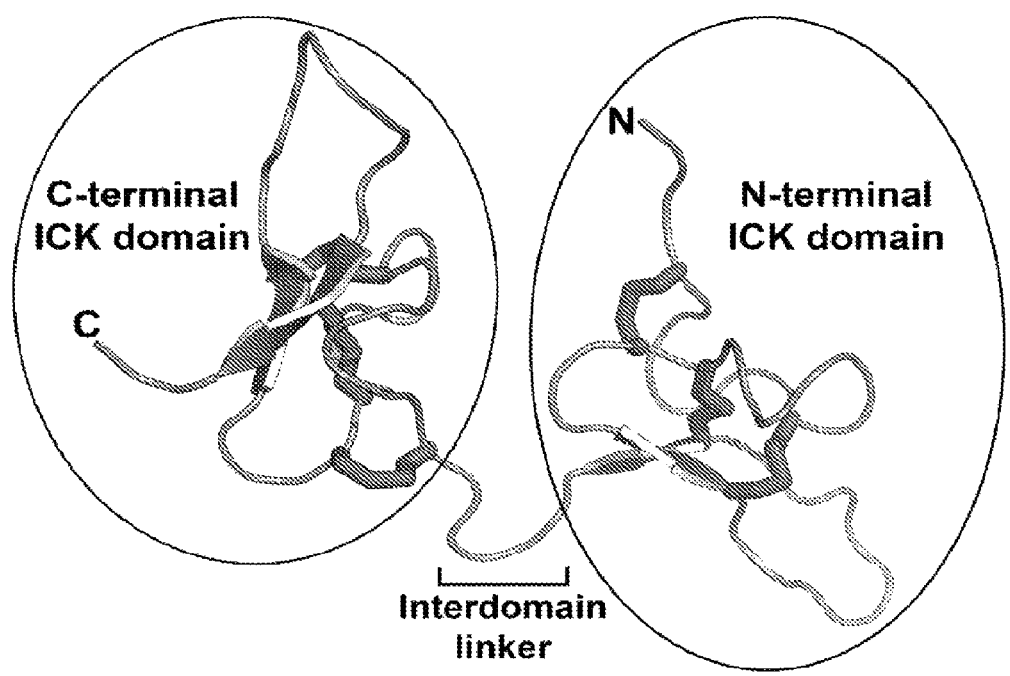
FIG. 8. Structure of Hi1a. Schematic of the three-dimensional structure of Hi1a determined using nuclear magnetic resonance (NMR) spectroscopy (first structure in the ensemble of 20 structures in Protein Data Bank accession 2N8F). The N- and C-terminal inhibitor cystine knot (ICK) domains are labelled as well as the interdomain linker. The labels "N" and "C" indicate the N- and C-terminus of the peptide, respectively. Thick tubes represent disulfide bonds (three in each ICK domain).

The structure of Hi1a determined using NMR revealed that it is comprised of two homologous inhibitor cystine knot (ICK) domains connected via a short and structurally well-defined linker (FIG. 8). Thus, Hi1a is a member of the recently described "double-knot" toxin family Atomic coordinates for the ensemble of Hi1a structures have been deposited in the Protein Data Bank (accession number 2N8F).

Figure 9:
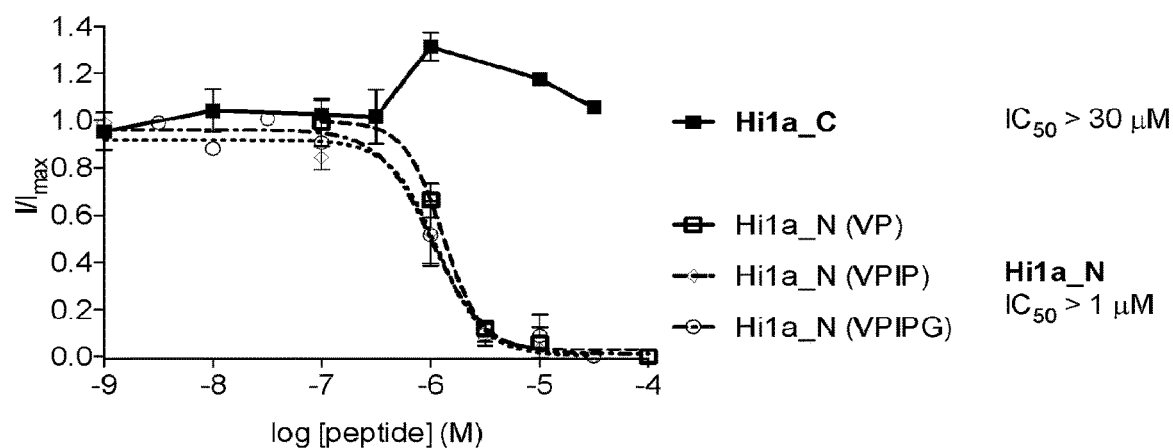
FIG. 9. Functional characterisation of individual Hi1a inhibitor cystine knot (ICK) domains. Top: Alignment of the amino acid sequences of the two ICK domains in Hi1a. Cysteine residues are highlighted by white text on a black background (Hi1a-N—SEQ ID NO:17; Hi1a-C—SEQ ID NO:36). Bottom: The graph shows concentration-effect curves for inhibition of rASIC1a by variants of the N-terminal ICK domain (Hi1a-N) and the C-terminal ICK domain (Hi1a-C) (number of experiments=5). $I/I_{max}$: test current/control current.

To determine whether either of the ICK domains of Hi1a are active in isolation, the N-terminal (Hi1a-N) and C-terminal (Hi1a-C) ICK domains were produced separately by expression in E. coli. Functional characterisation revealed that Hi1a_N can fully inhibit ASIC1a with an $IC_{50}$ of ~1 μM (i.e., ~1000-fold lower potency than either PcTx1 or full-length Hi1a). Unlike full length Hi1a, this effect was fully reversible (described below). There was no observed inhibitory effect for Hi1a_C up to 30 μM concentration (FIG. 9); however, at 1 μM, Hi1a_C induced minor potentiation of the current. Three constructs of Hi1a_N with varying C-terminal sequences were prepared (SEQ ID NOs:22 to 24). The concentration-effect curves for inhibition of rASIC1a by the three Hi1a_N constructs (FIG. 9) show that modifying the C-terminal sequence does not improve the activity of the N-terminal ICK domain of Hi1a.

Figure 10:
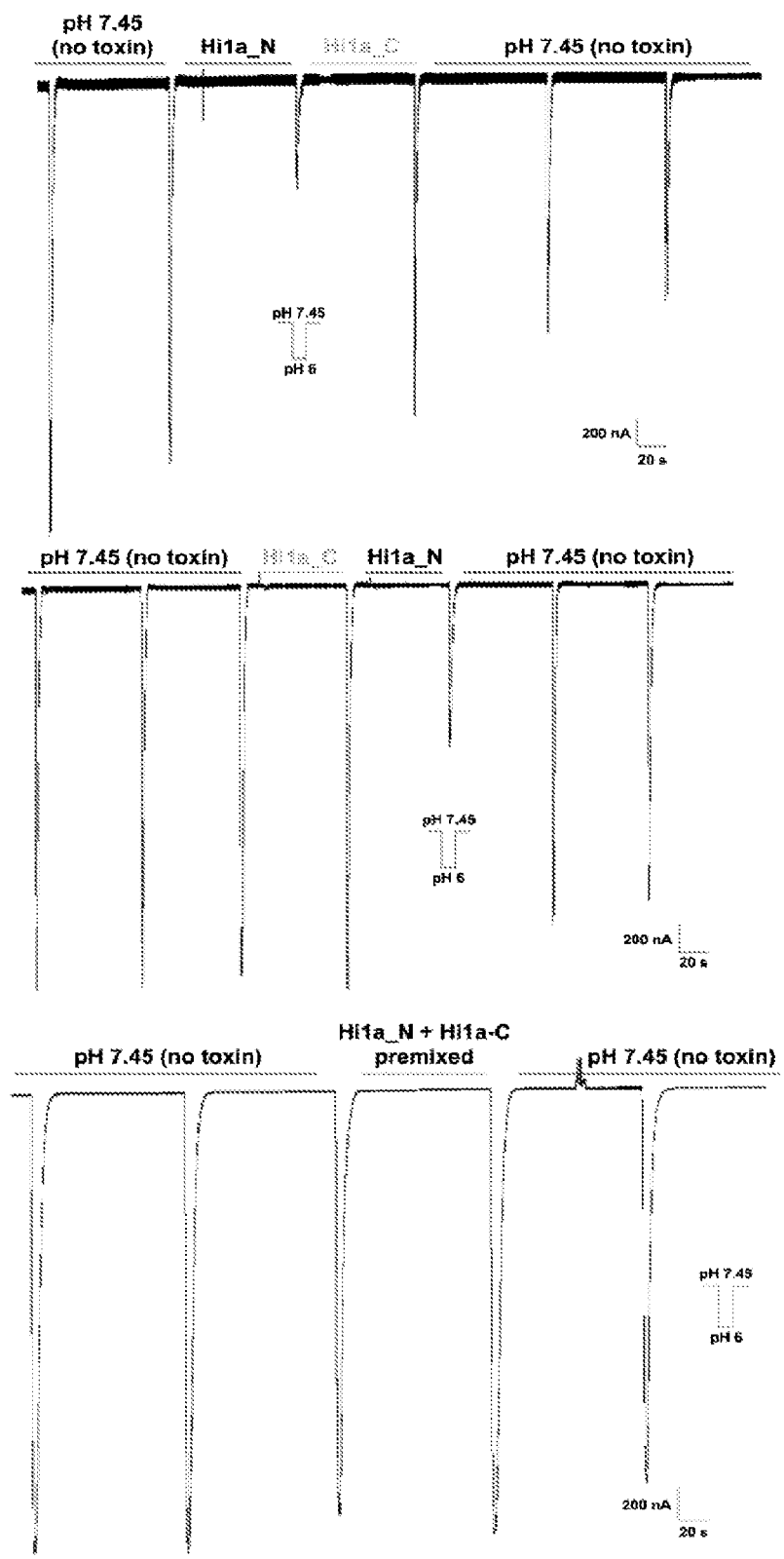
FIG. 10. Representative recordings from oocytes expressing rASIC1a. Whole-cell currents were elicited by a change in extracellular pH from 7.45 to 6.0, every 60 seconds. Oocytes expressing channels were exposed to peptides at pH 7.45 for 60 seconds. Top panel: Hi1a-N applied first at 3 µM; middle panel: Hi1a-C applied first at 10 µM; bottom panel: Both Hi1a-N and Hi1a-C premixed in solution at 3 µM and 10 µM respectively before applications.

FIG. 10 shows whole-cell recordings from oocytes expressing rASIC1a when Hi1a-N and Hi1a_C were co-applied or alternatively when Hi1a_N and Hi1a_C were applied sequentially, 60 seconds apart. These experiments revealed that rASIC1a inhibition by Hi1a_N is fully reversible, which can be seen as full recovery of rASIC1a currents 60 seconds after washout of the peptide. There was negligible inhibition by Hi1a_C at the chosen concentration (10 μM). Co-application of both peptides, or application of one followed 60 seconds later by the other, did not cause significant inhibition of rASIC1a over that caused by the N-terminal domain alone. Thus, covalent linkage of the two ICK domains is necessary for the unique inhibitory activity of Hi1a.

Example 6—Mutagenesis Studies

Hi1a Point Mutants

Mutagenesis studies were undertaken in order to identify key functional residues in Hi1a and to determine whether the spatial relationship between the ICK domains (dictated by the linker) is critical for Hi1a potency.

Figure 11:
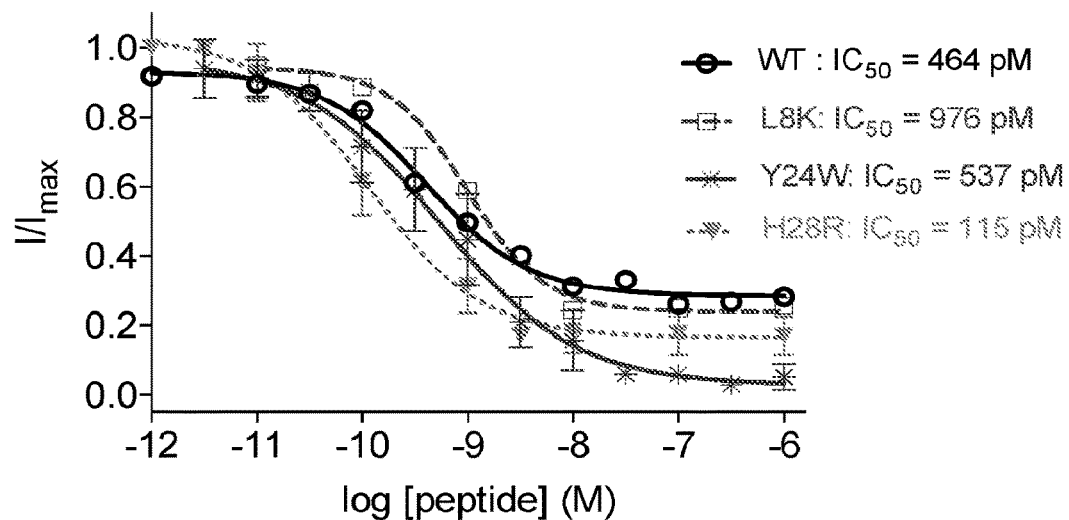
FIG. 11. Functional characterisation of Hi1a mutants. Top: Alignment of the amino acid sequences of PcTx1 (SEQ ID NO:15) and Hi1a (SEQ ID NO:16). The key pharmacophore residues K8, W24 and R28 in PcTx1 are replaced with Leu, Tyr and His, respectively, in Hi1a. These residues are highlighted in white text on a black background. The graph shows concentration-effect curves for inhibition of rASIC1a by wild-type Hi1a (WT) and the three Hi1a mutants (L8K, Y24W, and H28R). The corresponding $IC_{50}$ values are shown at right (number of experiments=5). test current/control current.

The N-terminal ICK domain of Hi1a is more homologous to PcTx1 than the C-terminal domain, but Hi1a does not contain several key pharmacophore residues (K8, W24 and R28) that were identified via mutagenesis of PcTx1 and a crystal structure of the PcTx1:chicken ASIC1 complex. To study the effect that alterations in these key pharmacophore residues has on the potency of Hi1a, the point mutations L8K, Y24W and H28R were introduced into Hi1a to make it more closely resemble PcTx1. The activity of these mutants on rASIC1a is shown in FIG. 11.

Unexpectedly, inserting PcTx1 pharmacophore residues into Hi1a had only a slight effect on the activity of Hi1a. The mutation H28R led to slightly increased potency (i.e., slightly lower $IC_{50}$ value) compared to wild-type Hi1a while L8K had little effect. Most notably, introduction of a Y24W mutation caused full inhibition of rASIC1a currents when applied at saturating concentrations. The effects of these three mutations (L8K, H28R, Y24W) could not have been predicted from previous studies of PcTx1. All three of the mutant Hi1a peptides appear to bind with very slow reversibility to rASIC1a, similar to wild-type Hi1a.

Engineered Peptides

Hi1a resembles two concatenated, non-identical copies of an ICK peptide with homology to PcTx1. In order to understand the unique mechanism of action and very slow reversibility of Hi1a, several peptides containing two ICK motifs with different linkers were designed and produced in E. coli (SEQ ID NOs:25 to 28). EP1 (SEQ ID NO:25) consists of two copies of PcTx1 joined by a linker as close to native PcTx1 as possible using the length of the linker in Hi1a. EP 2 (SEQ ID NO:26) is the same as EP 1 but with a Glu to Gly mutation in the linker to remove a negative charge and increase flexibility (this position is a Gly in the Hi1a linker). EP 3 (SEQ ID NO:27) is the same as Hi1a but with a modified linker in which the Ile-Pro sequence is replaced by five glycine residues, whilst in PcTx1/Hi1a_C (SEQ ID NO:28) the N-terminal ICK domain of Hi1a is replaced with PcTx1 and this chimeric peptide has a longer linker.

Figure 12:
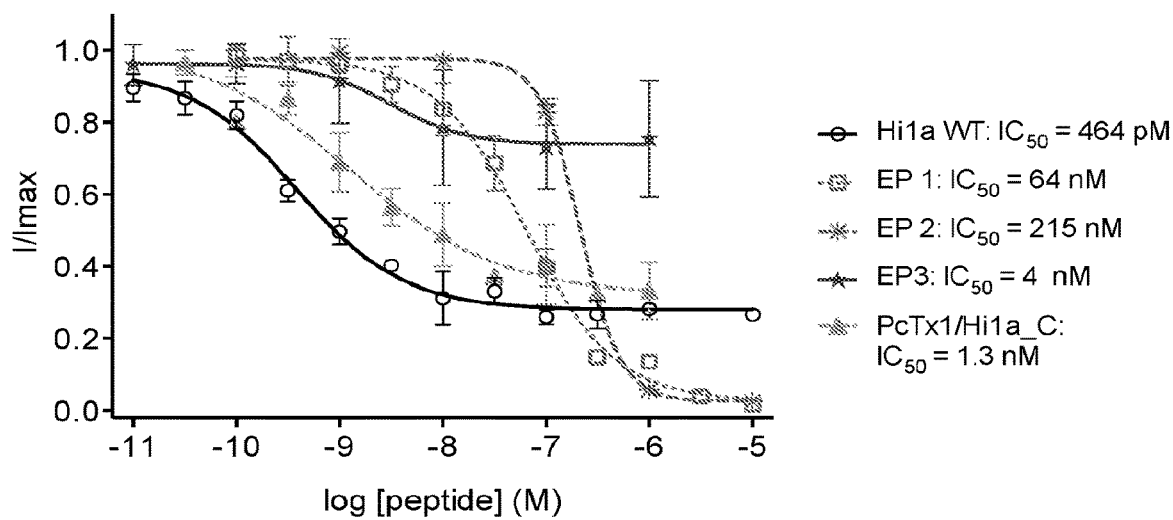
FIG. 12. Effect of Hi1a-like double ICK peptides on rASIC1a (number of experiments=5 for all). Top: Alignment of the amino acid sequences of Hi1a and the engineered Hi1a-like peptides (Hi1a WT—SEQ ID NO:16; EP 1—SEQ ID NO:37; EP 2—SEQ ID NO:38; EP 3—SEQ ID NO:39; PcTx1/Hi1a_C—SEQ ID NO:40). The linker region between the two ICK domains is highlighted with a grey box. The graph shows concentration-effect curves for inhibition of rASIC1a by wild-type Hi1a (Hi1a WT) and four Hi1a variants (EP 1, EP 2, EP 3, and PcTx1/Hi1a_C); corresponding $IC_{50}$ values are shown at right. $I/I_{max}$: test current/control current.

Functional characterisation of EP 1 and EP 2 revealed that these peptides inhibit rASIC1a with $IC_{50}$ values of 64 nM and 215 nM, respectively (FIG. 12), which corresponds to a ~200- and 500-fold increase in $IC_{50}$ (that is, decrease in potency) when compared to wild-type Hi1a (FIG. 2). Both EP 1 and EP 2, like PcTx1, induce full inhibition of ASIC1a currents. However, EP 3, which consists of the two ICK domains of Hi1a joined by a linker comprised of six glycine residues, did not inhibit rASIC1a currents by more than ~20% when applied at up to 1 µM. This demonstrates that the linker region is crucial for the activity of Hi1a. The activity of PcTx1/Hi1a_C is similar to Hi1a; it induces incomplete inhibition, albeit with 3-fold decrease in potency relative to Hi1a. Interestingly, all three inhibitory peptides (EP 1, EP 2 and PcTx1/Hi1a_C) appear to bind ASIC1a in an slowly reversible manner, similar to wild-type Hi1a.

Activity of Hi1d

Figure 13:
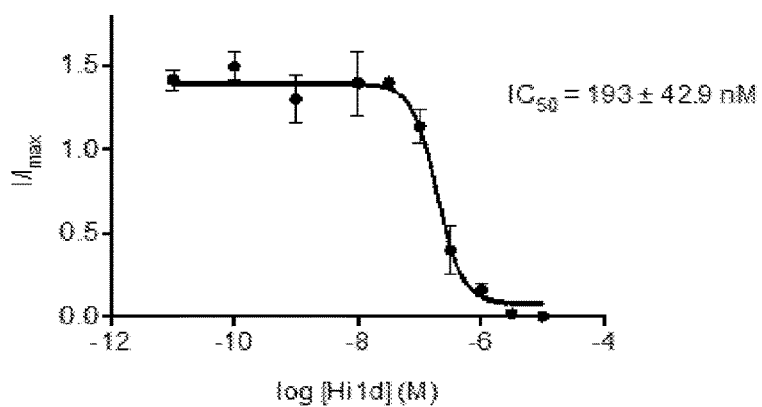
FIG. 13. Functional characterisation of recombinant Hi1d. Top: Alignment of the amino acid sequences of Hi1a (SEQ ID NO:16) and Hi1d (SEQ ID NO:31). Residues that are identical in the two peptides are highlighted in black on a grey background. The graph shows the concentration-effect curve for inhibition of rASIC1a by Hi1d (mean±SEM; number of experiments=6). $I/I_{max}$: test current/control current (mean±SEM; number of experiments=5).

Hi1d is another member of the Hi1a peptide family found in the venom-gland transcriptome of *Hadronyche infensa*. It has the same cysteine scaffold as Hi1a and the sequences of the two peptides are 63% identical. The N-terminal ICK domain of Hi1d is more similar to PcTx1 than is the N-terminal ICK domain of Hi1a, and Hi1d has a substantially different linker between the two ICK domains (8 residues, VPITQKIF, SEQ ID NO:41) than that of Hi1a (6 residues, VPIPGF, SEQ ID NO:42). Furthermore, there are several substantial differences in the C-terminal ICK domain (FIG. 13). To determine the functional significance of these differences, the activity of Hi1d was investigated using TEVC. Hi1d induced complete, concentration-dependent inhibition of rASIC1a currents with an $IC_{50}$ of 193 nM (FIG. 13). Moreover, the inhibition of ASIC1a by Hi1d was fully reversible within 60 seconds of washout.

A summary of the activity of the peptides tested is provided in Table 1.

TABLE 1

Summary of peptides examined for inhibition of ASIC1a.

| Peptide | $IC_{50}$ | % Residual Current | Rapidly reversible inhibition |
|---|---|---|---|
| Hi1a | rASIC1a-460 pM | rASIC1a-30% | No |
|  | hASIC1a-590 pM | hASIC1a-20% | No |
| Hi1a L8K | 976 pM | 30% | No |
| Hi1a Y24W | 537 pM | 0% | No |
| Hi1a H28R | 115 pM | 20% | No |
| Hi1d | 193 nM | 0% | Yes |
| EP 1 | 64 nM | 0% | No |
| EP 2 | 215 nM | 0% | No |
| EP 3 | >4 nM | 80% | N/A |
| PcTx1/Hi1a_C | 1.3 nM | ~35% | No |

Taken together, these results show that simply linking two identical ICK domains together is not sufficient to recapitulate the unique inhibitory activity of Hi1a at ASIC1a. The results also suggest that either the flexibility or chemical nature of the linker (or both) affects the peptide's ability to bind to and inhibit ASIC1a channels.

We therefore predict the following general structure for a neuroprotective peptide capable of specifically binding to acid sensing ion channel subtype 1a (ASIC1a):

$$X-L-Y \qquad (I)$$

wherein X and Y each represent a peptide sequence having an ICK fold and L is a linker.

The linker can be a bond, a non-amino acid-based chemical moiety, a single amino acid, or a peptide sequence. Where the linker is a single amino acid, it can be a naturally occurring amino acid or a synthetic, non-naturally occurring amino acid such as a chemical analogue of a corresponding naturally occurring amino acid. Alternatively, the linker can be a peptide sequence of at least 2, 3, 4, 5, 6, 7, 8, 9, 10, 11, 12, 13, 14, 15 or 16 amino acids. The amino acids of the sequence can be the same natural or non-natural amino acid, or each amino acid of the sequence can be independently selected from a naturally occurring amino acid or a synthetic, non-naturally occurring amino acid. Preferably, the linker is a peptide sequence of six naturally occurring amino acids.

X and Y can be different sequences or they can be the same sequence. Preferably, X and Y are different sequences, but both fold to form an ICK motif. Each X and Y is therefore preferably a sequence of about 30 to about 50 amino acids, even more preferably, about 30, 31, 32, 33, 34, 35, 36, 37, 38, 39 or 40 amino acids.

Example 7—Neuroprotection Assays

In vivo—i.c.v. Administration

The neuroprotective efficacy of Hi1a was assessed in a rat model of focal cerebral ischemia. In vivo experiments were conducted using a focal reperfusion model of stroke in conscious spontaneously hypertensive rats (SHR) as previously reported (McCarthy et al., *Neuropharmacology* 99, 650-657, 2015). Two 23-gauge stainless steel guide cannulae were stereotaxically implanted into anaesthetised animals (ketamine 75 mg/kg; xylazine 10 mg/kg; intraperitoneal) 5 days prior to stroke induction. The first cannula was implanted 3 mm dorsal to the right middle cerebral artery for stroke induction. The second cannula was implanted into the left lateral ventricle for drug administration.

After 5 days recovery, stroke was induced in conscious rats by inserting a 30-gauge injector protruding 3 mm below the previously implanted cannula. Endothelin-1 (20 pmol/µl) was administered at a rate of 0.2 µl every 30 s until animals exhibited behaviours previously correlated with stroke severity. Only animals that achieved a level 4 stroke were included in the study. Typical behaviours associated with a level 4 stroke include continuous ipsilateral circling, clenching, dragging, failure to extend the left contralateral forelimb, chewing, jaw flexing, and shuffling with forepaws.

Compared to models of middle cerebral artery occlusion (MCAO) achieved by surgical exposure of the artery, this model has the advantage of minimal surgical intervention in the brain, and the stroke is induced in the absence of anaesthetics, which can confound the results of drug studies (Callaway et al., 1999; Sharkey et al., 1993). Stroke-induced motor deficit was assessed by counting the number of foot faults made while rats traversed a gradually narrowing ledged beam (McCarthy et al., *Stroke* 40, 1482-1489, 2009). Animals were trained to traverse the beam on two consecutive days prior to pre-stroke assessment. For the neurological score, postural abnormalities were assessed by elevating the rat by the tail above a flat surface and grading the severity of thorax twisting and the angle of forelimb extension. Both indicators of neurological health are scored between 0 and 3, with a score of 0 corresponding to no twisting of the thorax or complete forelimb extension towards the flat surface. A score of 3 corresponds to severe thorax twisting and a failure to extend the forelimb. The score for thorax twisting and forelimb extension are summed to give a total possible score of 6, which represents severe neurological deficit. Both behavioural tests were performed prior to stroke, and at 24 and 72 h after stroke.

At 72 h post-stroke, rats were re-anaesthetised (ketamine 75 mg/kg; xylazine 10 mg/kg; intraperitoneal) and transcardially perfused with physiologically buffered saline. Brains were removed, snap frozen and sectioned (16 μm) at eight pre-determined forebrain levels (−3.20 mm to 6.8 mm) relative to bregma. Sections were imaged, and infarct volumes were measured using the ballistic light method and corrected for edema (McCarthy et al., Stroke 40, 1482-1489, 2009).

Figure 14:
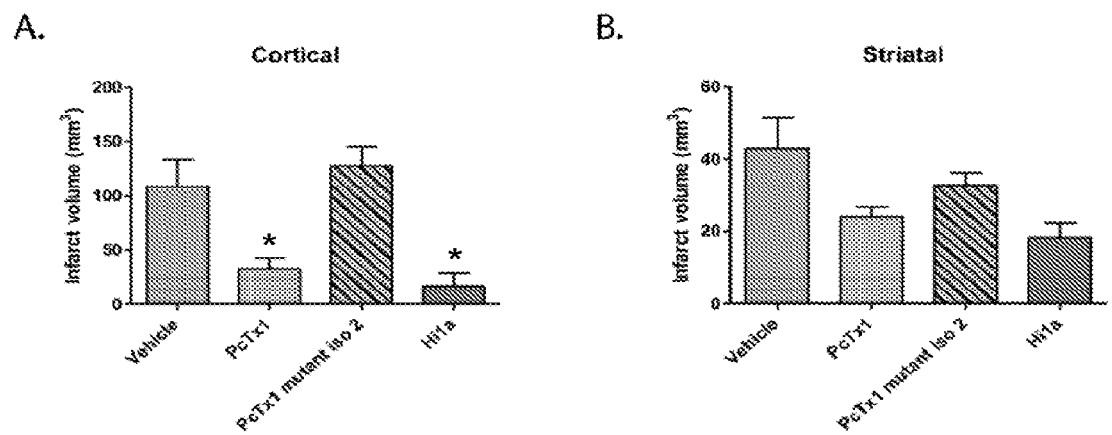
FIG. 14. SHR were given intracerebroventricular (i.c.v.) PcTx1 (1 ng/kg), a PcTx1 double mutant that is inactive on ASIC1a ("PcTx1 mutant iso 2"; 1 ng/kg), Hi1a (2 ng/kg) or vehicle (saline) two hours after stroke. PcTx1 and Hi1a both reduced infarct size in the (A) cortical (peri-infract zone) and (B) striatal (necrotic core) regions of the brain, but Hi1a was more effective. The inactive PcTx1 mutant had no effect on infarct size. Data points are mean±SEM (number of experiments=7). *$P<0.05$ versus vehicle (one-way ANOVA).

In one series of experiments, SHR were treated two hours after stroke induction with a single intracerebroventricular (i.c.v.) dose of Hi1a (2 ng/kg), PcTx1 (1 ng/kg), a double-mutant PcTx1 analogue (R27A/V32A="PcTx1 mutant iso 2"; McCarthy et al., 2015) that is inactive against ASIC1a (1 ng/kg), or saline (vehicle) using a 30-gauge injector protruding 3 mm below the previously implanted guide cannula. The doses of Hi1a and PcTx1 were chosen to give approximately equivalent molar concentrations as Hi1a is twice the molecular mass of PcTx1. Drugs were dissolved in saline and infused in a volume of 3 μl over 3 min. At 3 days after stroke, the brains were perfused, removed, then snap frozen and sectioned to determine the infarct size. The results, with data points as mean±standard error of mean (SEM) from experiments with seven animals, are shown in FIG. 14. Both PcTx1 and Hi1a caused a significant reduction in infarct volume in both the penumbral (cortical) region and ischemic (striatal) core, but Hi1a was more effective than PcTx1. The disarmed PcTx1 mutant was completely ineffective at reducing infarct volume.

In a separate series of experiments, Hi1a (2 ng/kg) was administered i.c.v. to SHR at 2, 4 or 8 hours after stroke induction. Motor-coordination (ledged beam test) and stroke-related postural abnormalities (neurological test) were evaluated at days 1 and 3 post-stroke. At 3 days after stroke, the brains were perfused, removed, then snap frozen and sectioned to determine the infarct size.

Figure 15:
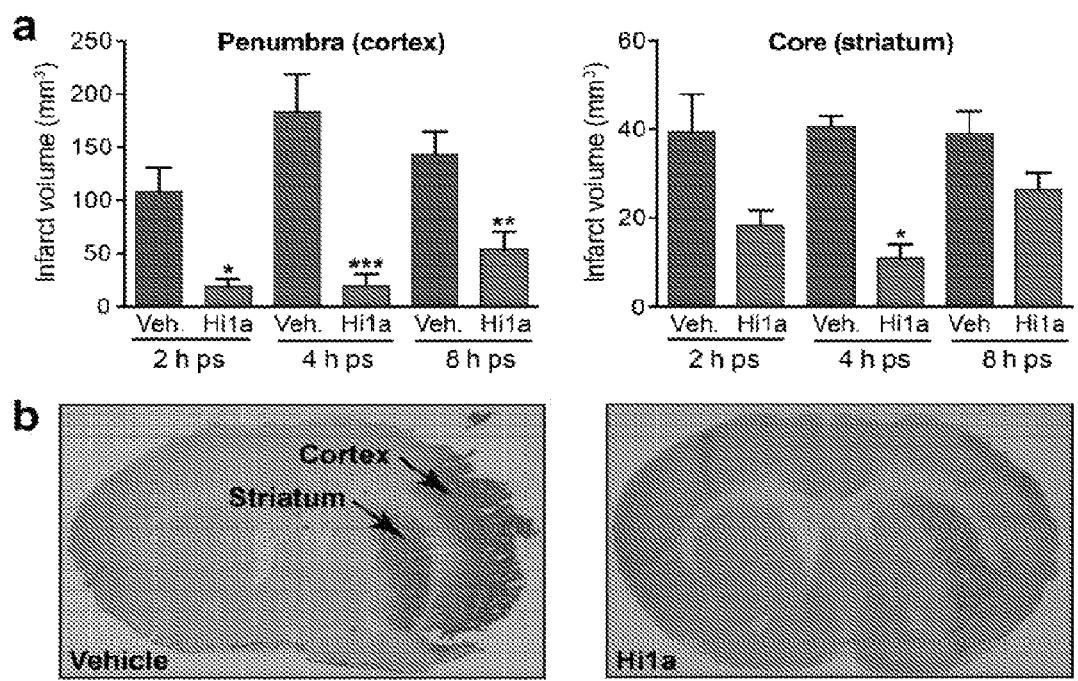
FIG. 15. Intracerebroventricular (i.c.v.) administration of Hi1a at 2, 4, or 8 hours post-stroke reduces infarct size in both the cortical (peri-infract zone) and striatal (necrotic core) regions. (a) Intracerebroventricular (i.c.v.) administration of vehicle (saline) or Hi1a (2 ng/kg) at 2, 4, or 8 hours post-stroke. Vehicle: 2 hours, number of experiments=10; 4 hours, number of experiments=7; 8 hours, number of experiments=9. Hi1a: 2 hours, number of experiments=5; 4 hours, number of experiments=7; 8 hours, number of experiments=10. Data points are mean±SEM. Volumes were measured at 72 hours post-stroke and corrected for edema. *$P<0.05$, $P<0.01$, *$P<0.001$ versus vehicle (one-way ANOVA). (b) Coronal sections showing typical infarcted (darker area) and non-infarcted regions from spontaneously hypertensive rats (SHR) treated i.c.v. with either vehicle or Hi1a (2 ng/kg) 8 hours after stroke.

FIG. 15a shows infarct volumes following i.c.v. administration of vehicle (saline) or Hi1a (2 ng/kg) at 2, 4 or 8 hours post-stroke (ps). A single dose of Hi1a (2 ng/kg) was sufficient to dramatically reduce infarct size by 63-83%. The coronal sections in FIG. 15b show typical infarcted and non-infarcted regions from SHR treated i.c.v. with either vehicle or Hi1a (2 ng/kg) 8 hours after stroke. Notably, Hi1a caused a reduction in infarct volume in the ischemic (striatal) core as well as the penumbral region (cortical or peri-infarct zone) at all time points.

Figure 16:
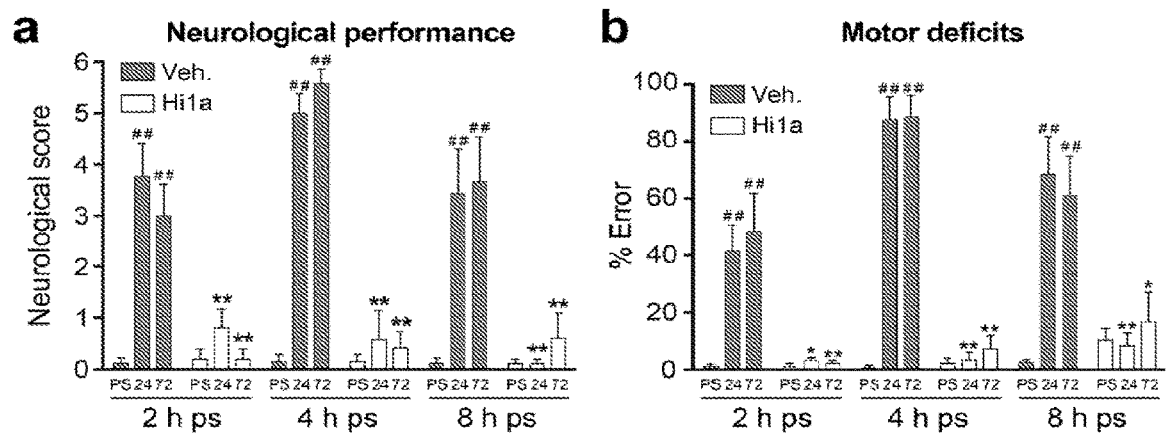
FIG. 16. Reduction in infarct size with Hi1a administration correlates with improved behavioural scores after stroke. (a) Neurological scores measured pre-stroke (PS) and 24 and 72 hours post-stroke (ps). Data points are mean±SEM. ##$p<0.01$ versus pre-stroke performance; **$p<0.01$ versus corresponding time in vehicle-treated group (two-way repeated measures ANOVA followed by Tukey post hoc tests). (b) Motor score (% error in ledged beam test) measured pre-stroke (PS) and 24 and 72 hours post-stroke. Data points are mean±SEM. ##$p<0.01$ versus pre-stroke performance; *$p<0.05$, **$p<0.01$ versus corresponding time in vehicle-treated group (two-way repeated measures ANOVA followed by Tukey post hoc tests).
Figure 17:
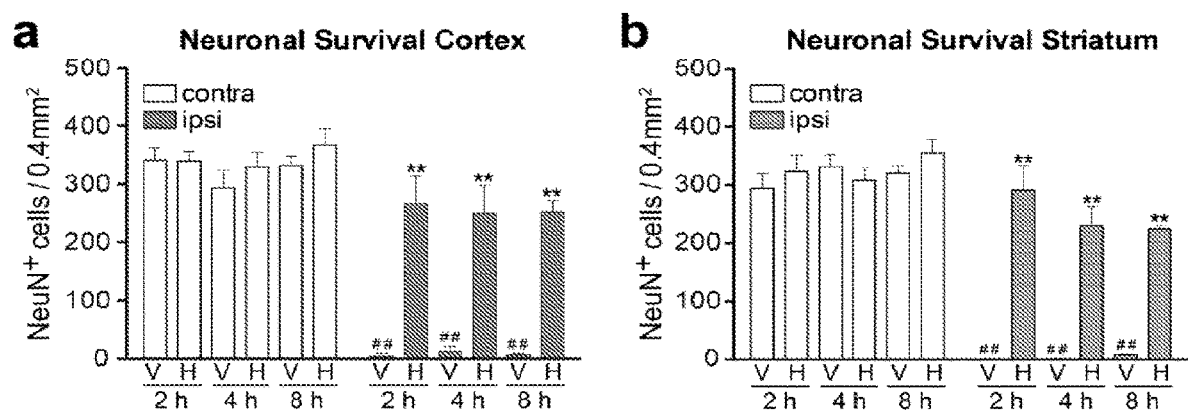
FIG. 17. The reduction in infarct size with Hi1a administration (FIG. 15) correlates with improved neuronal survival. Neuronal survival in the penumbral (cortical) and core (striatal) regions of damage was measured 72 hours post-stroke. Data are expressed as the number (mean±SEM) of NeuN-immunopositive (NeuN$^+$) cells per 0.4 mm$^2$ within the non-occluded (contralateral) and occluded (ipsilateral) hemispheres. **p<0.01 versus vehicle-treated group (ipsilateral side); ##p<0.01 versus matched region on non-infarcted hemisphere (two-way ANOVA followed by Tukey post hoc tests).

The reduction in infarct size caused by Hi1a administration was reflected symptomatically, with Hi1a-treated animals exhibiting markedly reduced neurological deficit (FIG. 16a) and motor impairment (FIG. 16b), and it is also correlated with preservation of neuronal architecture in both the penumbral and core regions of damage, as evidenced by intact neuronal staining as shown in FIGS. 17a and 17b.

In Vivo—Intranasal Administration

Figure 18:
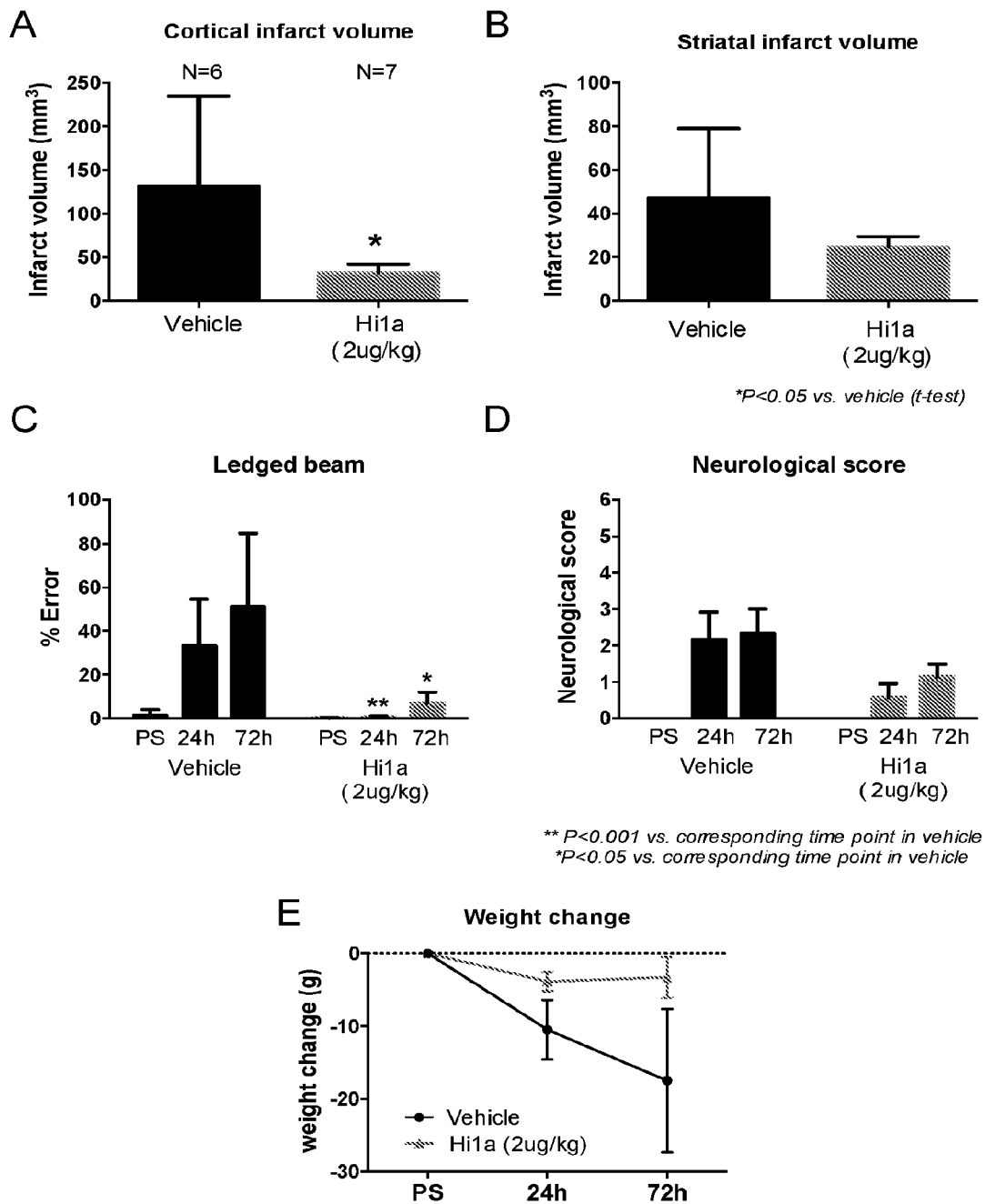
FIG. 18. Intranasal (i.n.) administration of Hi1a reduces infarct size in both the cortical (peri-infract zone) and striatal (necrotic core) regions. Compared with i.n. administration of vehicle, i.n. administration of Hi1a at a dose of 2 μg/kg four hours after stroke reduces infarct size in both (A) cortical and (B) striatal regions of the brain, reduces sensorimotor deficits measured using the ledged beam assay (C), improves overall neurological score (D) and minimises weight loss (E). Infarct volume was measured at 72 hours after stroke. Behavioural tests were carried out pre-stroke (PS) and 24 and 72 hours post-stroke. Data points are mean±SEM. Vehicle: number of experiments=6. Hi1a (2 μg/kg): number of experiments=7. *P<0.05 vs corresponding time point in vehicle, **P<0.001 vs corresponding time point in vehicle.

Four hours after stroke induction, SHR were treated with a single intranasal (i.n.) dose of Hi1a (2 μg/kg) or vehicle (saline). The Hi1a or vehicle was delivered i.n. in 3 μL delivered to the left nostril via a soft catheter inserted 6 mm into the nostril. Motor-coordination (ledged beam test) and stroke-related postural abnormalities (neurological test) were evaluated at 24 and 72 hours post-stroke. At 72 hours after stroke, the brains were perfused, removed, then snap frozen and sectioned to determine infarct size. The results are shown in FIG. 18.

Intranasal administration of Hi1a four hours after stroke induction dramatically reduced infarct size. Hi1a afforded protection not only in the cortical zone (FIG. 18A), but also in the striatal core (FIG. 18B). The preservation of brain tissue was also reflected symptomatically, with Hi1a-treated animals experiencing less motor impairment as judged by a ledged beam assay (FIG. 18C), reduced neurological deficit (FIG. 18D), and suffering less weight loss after stroke than untreated rats (FIG. 18E).

Therapeutic Uses

Acidosis occurs when the extracellular pH falls below 7.35. This is a common event in many pathophysiological conditions that affect the central and/or peripheral nervous system. Tissue injury (e.g., incisions or trauma), inflammation, arthritis, infection, ischemia, exercise and cancer all cause the local pH to decrease sufficiently (<7) to activate homomeric ASIC1a (Dube et al., 2009). In both rodents and humans, ASIC1a is highly expressed in sensory and central neurons, which makes them ideally placed to sense the acidosis associated with these conditions. Furthermore, the function of ASIC1a is substantially enhanced by extracellular mediators that are released during periods of ischaemia and inflammation (Deval and Lingueglia, 2015; Huang et al., 2015). These properties of ASIC1a makes this channel a potential drug target for several neurodegenerative and neuroinflammatory diseases.

Following an experimentally-induced traumatic injury in mice, the brain cortex becomes acidic, as observed in humans following brain trauma. The resulting acidosis activates ASIC1a, which contributes to secondary cell damage and neurological deficits. Genetic knockout of ASIC1a leads to reduced neurodegeneration after traumatic brain injury (Yin et al., 2013). Inhibition of ASIC1a using Hi1a may therefore provide a novel therapeutic approach to reduce neurological deficits following traumatic brain injury.

Epilepsy is a neurological disorder caused by hyperactivity of brain neurons. Even though the onset of seizures (and the ion channels involved) has been extensively studied, the molecular mechanism by which seizures are terminated remains unclear. It has been shown that excessive firing of action potentials reduces brain pH, which in turn halts the seizure (Somjen, 1984). Disrupting ASIC1a in mice causes more severe seizures, while overexpressing ASIC1a does not affect seizure onset, but shortens their duration (Ziemann et al., 2008). These data suggest that acidosis, and ASIC1a activation, limits seizure-like activity in the brain, and therefore identifies ASIC1a as a potential marker of seizure termination, opening new perspectives in the design of anti-epileptic drugs.

Huntington's disease (HD) is an autosomal dominant neurological disorder related to the expansion of a CAG repeat in the HD gene. This expansion causes misfolding of its gene product, huntingtin protein, resulting in muscle spasms and dementia. Aggregation of misfolded huntingtin in brain cells causes the formation of inclusion bodies, which disrupts normal neurotransmitters and eventually overall neuronal trafficking (Rubinsztein and Carmichael, 2003). HD is associated with acidification sufficient to activate ASIC1a in the CNS, which might contribute to the pathogenesis and formation of aggregates. Suppressing the expression of ASIC1a or its pharmacological inhibition in vivo enhances the activity of a specific proteasome, which reduces aggregation of huntingtin (Wong et al., 2008). Thus, ASIC1a is a potential new drug target for this debilitating disease.

Multiple sclerosis (MS) is an autoimmune disease in which the myelin sheath surrounding axons of the brain and spinal cord is damaged. This neuroinflammatory insult leads to axonal degeneration which in turn leads to progressive motor, sensory, and cognitive disabilities (Filippi, 2011). A recent study on both animal models and human tissue identified an increased level of ASIC1a expression in glial cells and axons from MS lesions (Vergo et al., 2011). Furthermore, ASIC1$^{-/-}$ mice were found to present symptoms of much lower severity in models of MS. These findings suggest that activation of ASIC1a can underlie the neurodegeneration seen in MS and that ASIC1a inhibitors have the potential to provide both neuro- and myelo-protective benefits in MS.

Spinal cord injury leads to local acidosis from tissue trauma and ischaemia, which results in secondary cell death. ASIC1a is over-expressed in injured spinal cord nerves and support cells, and it has been shown to play a substantial role in the secondary damage and resulting loss of function (Hu et al., 2011). Inhibition of ASIC1a is neuroprotective in spinal cord injury (Hu et al., 2011; Koehn et al., F1000Research, 2016), and therefore novel inhibitors of ASIC1a such as Hi1a have potential for treatment of spinal cord injury.

It is to be appreciated that conditions other than those described above may be caused by ASIC1a activity or contributed to by ASIC1a activity, and so the peptide described by formula (I) may be used in the prophylaxis or treatment of those other conditions. That is, the peptide may function therapeutically other than as a neuroprotective agent.

Routes of Administration and Doses

ASIC1a is a therapeutic target with a temporal window that is in keeping with the clinical presentation after an ischemic event. Pure Hi1a peptide yielded excellent neuroprotection of both the striatal (core) and cortical (peri-infarct) region in rats when administered via either i.c.v. injection or intranasal administration up to 4 hours after induction of stroke. Therefore i.c.v. or intranasal administration may be used as route of administration.

Under normal circumstances the entry of ions, small molecules and proteins to the brain is tightly regulated by the blood brain barrier (BBB). However, pathological insults to the brain, such as stroke or traumatic brain injury, result in a rapid increase in the permeability of the BBB. Following traumatic brain injury molecules from 286 to 10,000 Da (Hi1a is ~8700 Da) can enter the brain freely for up to four days (Habgood et al., 2007). Similarly, following ischemia there is a biphasic opening of the BBB (mediated by the activation of different groups of metalloproteinases) commencing within hours of insult and lasting up to 3 days (Yang and Rosenberg, 2011). Thus, in a clinical post-stroke setting, in the presence of a compromised BBB, intravenous (i.v.) administration of Hi1a may result in neuroprotection.

In the preferred case, a method of peptide drug delivery that bypasses hepatic metabolism and the BBB entirely could be used. Intranasal (i.n.) administration is non-invasive, leads to uptake directly to the brain, and it avoids both hepatic metabolism and the BBB. There are several intranasally administered peptide drugs already on the market (Casettari and Ilium, 2014). Intranasal delivery of PcTx1 crude venom was previously shown to provide neuroprotection up to 4 hours post-stroke (Pignataro et al., 2007), and we have demonstrated that intranasal delivery of Hi1a alone up to at least four hours post-stroke provides high levels of neuroprotection (FIG. 18). Thus, in a clinical post-stroke setting, therapeutic application of Hi1a and modifications thereof could be achieved via i.c.v., i.n., or i.v. administration.

i.c.v. administration of a functionally-relevant dose of pure Hi1a in conscious SHR rats is highly neuroprotective when given post-stroke. The dose of Hi1a used in the example (2 ng/kg i.c.v.) equates to a brain concentration of ~1.2 nM, which should inhibit brain ASIC1a activity by ~80% based on in vitro data. Thus i.c.v. dosing would preferably be in the range of 1-10 ng/kg.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

CITATION LIST

Bendtsen J D et al., *J Mol Biol*, 2004, 340(4), 783-795
Besancon E et al., *Trends Pharmacol Sci*, 2008, 29:268-275
Bohlen C J et al., *Cell*, 2010, 141:834-845
British Pharmacopoeia (BP)
Bundy B C and Swartz J R, *J Biotechnol*, 2011, 154:230-239
Callaway J et al., *Stroke*, 1999, 30:2704-2712
Casettari L and Ilium L, *Journal of Controlled Release*, 2014, 190:189-200
Chen X et al., *J Gen Physiol*, 2005, 126:71-79
Chevreux B et al., *Genome Res*, 2004, 14:1147-1159
Conesa A et al., *Bioinformatics*, 2005, 21(18):3674-6
Deval E and Lingueglia E, *Neuropharmacology*, 2015, doi:10.1016/j.neuropharm.2015.02.009
Drummond A J et al., Geneious v.4, 2011
Dube G R et al., *Curr Pharm Design*, 2009, 15:1750-1766
Filippi M, *Nat Rev Neurol*, 2011, 7:74-75
Green M R and Sambrook J, *Molecular Cloning: A Laboratory Manual*, 4th Edition, Cold Spring Harbor Laboratory, 2012
Gründer S and Chen X, *Int J Physiol Pathophysiol Pharmacol*, 2010, 2:73-94
Habgood M D et al., *Eur J Neurosci*, 2007, 25(1):231-238
Herzig V et al., *Nucl Acids Res*, 2011, 39 (suppl 1):D653-D657
Hu R et al., *Ann Surg*, 2011, 254(2):353-62
Huang et al., *Neuropharmacology*, 2015, 94:42-48
Isaev N K et al., *Biochemistry (Mosc)*, 2008, 73:1171-1175
Jasti J et al., *Nature*, 2007, 449:316-323

Kim D-M and Swartz J R, *Biotechnol Bioeng,* 2004, 85:122-129

Klint J K et al., *PLoS ONE,* 2013, 8(5):e63865

Koehn L M et al., *F1000Research,* 2016

Krishtal O, *Trends Neurosci,* 2003, 26:477-483

Leng T D et al., *Acta Pharmacol Sin,* 2013, 34:33-38

Li M et al., *J Cereb Blood Flow Metab,* 2010, 30:1247-1260

Liu R et al., *Neurol Res,* 2012, 34:331-337

McCarthy et al., *Stroke,* 2009, 40:1482-1489

McCarthy C A et al., *Neuropharmacology,* 2015, 99:650-657

Milne I et al., *Bioinformatics,* 2010, 26(3):401-402

Moskowitz M A et al., *Neuron,* 2010, 67:181-198

Pandey R et al., *BMC Research Notes,* 2010, 3:3

Pignataro G et al., *Brain,* 2007, 130:151-158

Rowe R C, Sheskey P J, Quinn M E (Ed.), 'Handbook of Pharmaceutical Excipients', 6th Ed., London: Pharmaceutical Press (2009)

Rubinsztein D C and Carmichael J, *Expert Rev Mol Med,* 2003, 5:1-21

Sachev D and Chirgwin J M, *Methods Enzym,* 2000, 326:312-321

Senes S, 'How we manage stroke in Australia', Australian Institute of Health and Welfare, Canberra, Australia, 2006

Sharkey J et al., *J Cerebral Blood Flow,* 1993, 13:865-871

Sherwood T et al., *J Biol Chem,* 2009, 248:27899-27907

Smith D B, *Methods Enzym,* 2000, 326:254-270

Somjen G G, Brain Res, 1984, 311:186-188

Sweetman S (Ed.), 'Martindale: The complete drug reference.' London: Pharmaceutical Press, 37th Ed., (2011)

United States Pharmacopeia and National Formulary (USP-NF)

Vergo S et al., *Brain,* 2011, 134:571-584

Wang Y Z et al., *Mol Neurobiol,* 2011, 44:350-358

Wemmie J A et al., *Trends Neurosci,* 2006, 29:578-586

Wong H K et al., *Hum Mol Genet,* 2008, 17:3223-3235

Woodruff T M et al., *Mol Neurodegener,* 2011, 6:11

Xiong Z G et al., *Cell,* 2004, 118:687-698

Xiong Z G et al., *Front Biosci,* 2007, 12:1376-1386

Yang Y and Rosenberg G A, *Stroke,* 2011, 42(11):3323-8

Yin T et al., *PLoS ONE,* 2013, 8(8):e72379

Ziemann A E et al., *Nat Neurosci,* 2008, 11:816-822

The invention claimed is:

1. An isolated, synthetic, or recombinant peptide, wherein the peptide comprises an amino acid sequence consisting of an N terminal serine residue and any one of SEQ ID NOs: 18, 19, and 20.

2. A pharmaceutical composition comprising a therapeutically effective amount of the isolated, synthetic, or recombinant peptide of claim 1.

3. The pharmaceutical composition of claim 2, further comprising at least one pharmaceutically acceptable diluent, adjuvant, excipient, buffer, stabiliser, isotonicising agent, preservative, or anti-oxidant.

4. The pharmaceutical composition of claim 3, further comprising at least one delivery enhancer to assist with transport of the peptide across the blood brain barrier (BBB), wherein the at least one delivery enhancer is selected from the group consisting of lipids, polymers, liposomes, emulsions, and nanoparticles.

5. An isolated, synthetic, or recombinant peptide, wherein the peptide consists of
   a) an amino acid sequence consisting of an N terminal serine residue and any one of SEQ ID NOs: 18, 19, and 20, or
   b) SEQ ID NO: 19.

6. A method for treatment of a disease or condition in a subject, wherein the disease or condition is caused by ASIC1a activity or contributed by ASIC1a activity, the method comprising: administering a therapeutically effective amount of at least one isolated, synthetic, or recombinant peptide to the subject, wherein the peptide comprises an amino acid sequence selected from the group consisting of:
   (a) an amino acid sequence consisting of an N terminal serine residue and any one of SEQ ID NOs: 18, 19, and 20;
   (b) the amino acid sequence of SEQ ID NO: 19;
   (c) an amino acid sequence consisting of an N terminal serine residue and an amino acid sequence that shares at least 90% sequence identity with any one of SEQ ID NOs: 18, 19, and 20; and
   (d) an amino acid sequence that shares at least 90% sequence identity with SEQ ID NO: 19,
wherein the amino acid sequence comprises six cysteine residues covalently joined in pairs to form three disulfide bonds, such that the amino acid sequence comprises one ICK motif, and wherein said peptide is capable of specifically binding to acid sensing ion channel subtype 1a (ASIC1a).

7. The method of claim 6, wherein the isolated, synthetic or recombinant peptide comprises
   (a) an amino acid sequence consisting of an N terminal serine residue and any one of SEQ ID NOs: 18, 19, and 20; or
   (b) SEQ ID NO: 19.

8. The method of claim 6, wherein the peptide comprises
   (a) an amino acid sequence consisting of an N terminal serine residue and the amino acid sequence of SEQ ID NO: 19; or
   (b) SEQ ID NO: 19.

9. The method of claim 6, wherein the peptide comprises an amino acid sequence consisting of an N terminal serine residue and the amino acid sequence of SEQ ID NO: 18 or SEQ ID NO: 20.

10. The method of claim 6, wherein the disease or condition caused by ASIC1a activity or contributed to by ASIC1a activity is an ischemic disease.

11. The method of claim 6, wherein the disease or condition is stroke.

12. The method of claim 6, wherein the disease or condition is neuronal damage following stroke.

13. The method of claim 6, wherein the isolated, synthetic or recombinant peptide is administered via intracerebroventricular (i.c.v.) administration, intravenous (i.v.) administration, intraarterial (i.a.), or intranasal (i.n.) administration.

14. The method of claim 10, wherein the ischemic disease is cardiac ischemia.

15. The method of claim 6, wherein the disease or condition is angina associated with cardiac ischemia.

16. The method of claim 6, wherein the disease or condition is spinal cord injury.

17. The method of claim 16, wherein the spinal cord injury is associated with multiple sclerosis (MS).

18. The method of claim 6, wherein administering the peptide comprises administering a pharmaceutical composition comprising the peptide.

19. The method of claim 18, wherein the pharmaceutical composition comprises at least one pharmaceutically acceptable diluent, adjuvant, excipient, buffer, stabiliser, isotonicising agent, preservative, or anti-oxidant.

20. The method of claim 19, wherein the pharmaceutical composition further comprises at least one delivery enhancer to assist with transport of the peptide across the blood brain barrier (BBB), wherein the at least one delivery enhancer is selected from the group consisting of lipids, polymers, liposomes, emulsions, and nanoparticles.

* * * * *

SEQUENCE LISTING

```
<160> NUMBER OF SEQ ID NOS: 42

<210> SEQ ID NO 1
<211> LENGTH: 390
<212> TYPE: DNA
<213> ORGANISM: Hadronyche infensa

<400> SEQUENCE: 1
atgaaatttc caaacttcga agtaatgctt cttctggtgt ggtctttaac gctttatgca    60
gttggtgatg caaaatatga agatttattg aaaaatgctt tagatgcaaa gttattgaat   120
gcatttgtgg aaacgattca attaaaaagc catgggaaga gaaatgagtg cataaggaaa   180
tggttgtctt gtgttgatcg gaaaaatgat tgctgtgagg ggctcgaatg ctataagagg   240
cgacattcgt tcgaagtatg tgtacccatt ccgggattct gcttagtaaa gtggaagcaa   300
tgcgatggac gagaacggga ttgctgcgca ggtcttgaat gctggaagag gagtggaaat   360
aagtcctcag tctgtgcacc gattacatga                                    390

<210> SEQ ID NO 2
<211> LENGTH: 129
<212> TYPE: PRT
<213> ORGANISM: Hadronyche infensa

<400> SEQUENCE: 2

Met Lys Phe Pro Asn Phe Glu Val Met Leu Leu Leu Val Trp Ser Leu
1               5                   10                  15

Thr Leu Tyr Ala Val Gly Asp Ala Lys Tyr Glu Asp Leu Leu Lys Asn
            20                  25                  30

Ala Leu Asp Ala Lys Leu Leu Asn Ala Phe Val Glu Thr Ile Gln Leu
        35                  40                  45

Lys Ser His Gly Lys Arg Asn Glu Cys Ile Arg Lys Trp Leu Ser Cys
    50                  55                  60

Val Asp Arg Lys Asn Asp Cys Cys Glu Gly Leu Glu Cys Tyr Lys Arg
65                  70                  75                  80

Arg His Ser Phe Glu Val Cys Val Pro Ile Pro Gly Phe Cys Leu Val
                85                  90                  95

Lys Trp Lys Gln Cys Asp Gly Arg Glu Arg Asp Cys Cys Ala Gly Leu
```

```
              100                 105                 110
Glu Cys Trp Lys Arg Ser Gly Asn Lys Ser Ser Val Cys Ala Pro Ile
        115                 120                 125
Thr
```

<210> SEQ ID NO 3
<211> LENGTH: 390
<212> TYPE: DNA
<213> ORGANISM: Hadronyche infensa

<400> SEQUENCE: 3

```
atgaaatttc caaacttcga agtaatgctt cttctggtgt ggtctttaac gctttatgca    60
gttggtgatg caaaatatga agatttattg aaaaatgctt tagatgcaaa gttatcgaat   120
gcatttgtgg aaacgattca attaaaaagc catgggaaga gaaatgagtg cataaggaaa   180
tggttgtctt gtgttgatcg gaagaatgat tgctgtgagg ggctcgaatg ctataagagg   240
cgacattcgt tcgaagtatg tgtacccatt ccgggattct gcttagtaaa gtggaagcaa   300
tgcgatggac gagaacggga ttgctgccca ggtcttgaat gctggaagag gagtggaaat   360
aagtcctcag tctgtgcacc aattacatga                                    390
```

<210> SEQ ID NO 4
<211> LENGTH: 129
<212> TYPE: PRT
<213> ORGANISM: Hadronyche infensa

<400> SEQUENCE: 4

```
Met Lys Phe Pro Asn Phe Glu Val Met Leu Leu Leu Val Trp Ser Leu
1               5                   10                  15
Thr Leu Tyr Ala Val Gly Asp Ala Lys Tyr Glu Asp Leu Leu Lys Asn
            20                  25                  30
Ala Leu Asp Ala Lys Leu Ser Asn Ala Phe Val Glu Thr Ile Gln Leu
        35                  40                  45
Lys Ser His Gly Lys Arg Asn Glu Cys Ile Arg Lys Trp Leu Ser Cys
    50                  55                  60
Val Asp Arg Lys Asn Asp Cys Cys Glu Gly Leu Glu Cys Tyr Lys Arg
65                  70                  75                  80
Arg His Ser Phe Glu Val Cys Val Pro Ile Pro Gly Phe Cys Leu Val
                85                  90                  95
Lys Trp Lys Gln Cys Asp Gly Arg Glu Arg Asp Cys Cys Pro Gly Leu
            100                 105                 110
Glu Cys Trp Lys Arg Ser Gly Asn Lys Ser Ser Val Cys Ala Pro Ile
        115                 120                 125
Thr
```

<210> SEQ ID NO 5
<211> LENGTH: 456
<212> TYPE: DNA
<213> ORGANISM: Hadronyche infensa

<400> SEQUENCE: 5

```
atgaaactca ggatcacgct tgctctgaca tctgtgctgg cattttgcgt ctttggagat    60
aaagaaaatg aaaatttaat ggaaaatctt ttggaagacg acctattgga tattttcacg   120
gacgctattc atatggaacg ccaagaaaca aatcaggagt gcatagcgaa atggaaatca   180
tgcgctggca gaaaactgga ttgttgtgaa ggtcttgagt gctggaagag gagatgggga   240
```

```
catgaagtgt gcgttccaat tacacaaaag attttactgt ttagaaaagt ggaaaagtca      300
tgttttgaga ggaaatatga ttgctgtgaa gaacttgaat gctgggagag gagaggaaat      360
aagacaccca gtatgcgcac caaagcagta aggtcagtca gtggtcatga ggctctcagt      420
gttgcgctcc tcaaaacttg tatacattac aaataa                                456
```

```
<210> SEQ ID NO 6
<211> LENGTH: 151
<212> TYPE: PRT
<213> ORGANISM: Hadronyche infensa

<400> SEQUENCE: 6

Met Lys Leu Arg Ile Thr Leu Ala Leu Thr Ser Val Leu Ala Phe Cys
1               5                   10                  15

Val Phe Gly Asp Lys Glu Asn Glu Asn Leu Met Glu Asn Leu Leu Glu
                20                  25                  30

Asp Asp Leu Leu Asp Ile Phe Thr Asp Ala Ile His Met Glu Arg Gln

```
Val Phe Gly Asp Lys Glu Lys Glu Asn Leu Met Glu Asn Leu Leu Glu
             20                  25                  30

Asp Asp Leu Leu Asp Ile Phe Thr Asp Ala Ile His Met Glu Arg Gln
                 35                  40                  45

Glu Thr Asn Gln Glu Cys Ile Ala Lys Trp Lys Ser Cys Ala Gly Arg
 50                  55                  60

Lys Leu Asp Cys Cys Glu Gly Leu Glu Cys Trp Lys Arg Arg Trp Gly
 65                  70                  75                  80

His Glu Val Cys Val Pro Ile Thr Gln Lys Ile Phe Cys Leu Glu Lys
                 85                  90                  95

Trp Lys Ser Cys Phe Glu Arg Lys Tyr Asp Cys Cys Glu Glu Leu Glu
                100                 105                 110

Cys Trp Glu Arg Arg Gly Asn Lys His Pro Val Cys Ala Pro Lys Gln
            115                 120                 125
```

<210> SEQ ID NO 9
<211> LENGTH: 390
<212> TYPE: DNA
<213> ORGANISM: Hadronyche infensa

<400> SEQUENCE: 9

```
atgaaatttc caaacttcga agtaatgctt cttctggtgt ggtctttaac gctttatgca      60
gttggtgatg caaaatatga agatttattg aaaaatgctt tagatgcaaa gttatcgaat     120
gcatttgtgg aaacgattca attaaaaagc catgggaaga gaatgagtg cataaggaaa      180
tggttgtctt gtgttgatcg gaaaaatgat tgctgtgagg ggctcgaatg ctataagagg     240
cgacattcgt tcgaagtatg tgtacccatt ccgggattct gcttagtaaa gtggaagcaa     300
tgcgatggac gagaacggga ttgctgcgca ggtcttgaat gctggaagag gagtggaaat     360
aagtcctcag tctgtgcacc aattgcatga                                      390
```

<210> SEQ ID NO 10
<211> LENGTH: 129
<212> TYPE: PRT
<213> ORGANISM: Hadronyche infensa

<400> SEQUENCE: 10

```
Met Lys Phe Pro Asn Phe Glu Val Met Leu Leu Val Trp Ser Leu
 1               5                  10                  15

Thr Leu Tyr Ala Val Gly Asp Ala Lys Tyr Glu Asp Leu Leu Lys Asn
             20                  25                  30

Ala Leu Asp Ala Lys Leu Ser Asn Ala Phe Val Glu Thr Ile Gln Leu
                 35                  40                  45

Lys Ser His Gly Lys Arg Asn Glu Cys Ile Arg Lys Trp Leu Ser Cys
 50                  55                  60

Val Asp Arg Lys Asn Asp Cys Cys Glu Gly Leu Glu Cys Tyr Lys Arg
 65                  70                  75                  80

Arg His Ser Phe Glu Val Cys Val Pro Ile Pro Gly Phe Cys Leu Val
                 85                  90                  95

Lys Trp Lys Gln Cys Asp Gly Arg Glu Arg Asp Cys Cys Ala Gly Leu
                100                 105                 110

Glu Cys Trp Lys Arg Ser Gly Asn Lys Ser Ser Val Cys Ala Pro Ile
            115                 120                 125

Ala
```

<210> SEQ ID NO 11

-continued

```
<211> LENGTH: 390
<212> TYPE: DNA
<213> ORGANISM: Hadronyche infensa

<400> SEQUENCE: 11
atgaaatttc caaacttcga agtaatgctt cttctggtgt ggtctttaac gctttatgca        60
gttggtgatg caaatatga agatttattg aaaaatgctt tagatgcaaa gttatcgaat       120
gcatttgtgg aaacgattca attaaaaagc catgggaaga ga

```
                1               5                   10                  15
Asp Cys Cys Glu Gly Leu Glu Cys Tyr Lys Arg Arg His Ser Phe Glu
                    20                  25                  30

Val Cys Val Pro Ile Pro Gly Phe Cys Leu Val Lys Trp Lys Gln Cys
                35                  40                  45

Asp Gly Arg Glu Arg Asp Cys Cys Ala Gly Leu Glu Cys Trp Lys Arg
        50                  55                  60

Ser Gly Asn Lys Ser Ser Val Cys Ala Pro Ile Thr
65                  70                  75

<210> SEQ ID NO 15
<211> LENGTH: 40
<212> TYPE: PRT
<213> ORGANISM: Psalmopeous cambridgei

<400> SEQUENCE: 15

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Ser Phe Glu Val
                20                  25                  30

Cys Val Pro Lys Thr Pro Lys Thr
            35                  40

<210> SEQ ID NO 16
<211> LENGTH: 75
<212> TYPE: PRT
<213> ORGANISM: Hadronyche infensa

<400> SEQUENCE: 16

Asn Glu Cys Ile Arg Lys Trp Leu Ser Cys Val Asp Arg Lys Asn Asp
1               5                   10                  15

Cys Cys Glu Gly Leu Glu Cys Tyr Lys Arg Arg His Ser Phe Glu Val
                20                  25                  30

Cys Val Pro Ile Pro Gly Phe Cys Leu Val Lys Trp Lys Gln Cys Asp
                35                  40                  45

Gly Arg Glu Arg Asp Cys Cys Ala Gly Leu Glu Cys Trp Lys Arg Ser
        50                  55                  60

Gly Asn Lys Ser Ser Val Cys Ala Pro Ile Thr
65                  70                  75

<210> SEQ ID NO 17
<211> LENGTH: 37
<212> TYPE: PRT
<213> ORGANISM: Hadronyche infensa

<400> SEQUENCE: 17

Asn Glu Cys Ile Arg Lys Trp Leu Ser Cys Val Asp Arg Lys Asn Asp
1               5                   10                  15

Cys Cys Glu Gly Leu Glu Cys Tyr Lys Arg Arg His Ser Phe Glu Val
                20                  25                  30

Cys Val Pro Ile Pro
            35

<210> SEQ ID NO 18
<211> LENGTH: 35
<212> TYPE: PRT
<213> ORGANISM: Hadronyche infensa

<400> SEQUENCE: 18
```

```
Asn Glu Cys Ile Arg Lys Trp Leu Ser Cys Val Asp Arg Lys Asn Asp
1               5                   10                  15

Cys Cys Glu Gly Leu Glu Cys Tyr Lys Arg Arg His Ser Phe Glu Val
            20                  25                  30

Cys Val Pro
        35
```

<210> SEQ ID NO 19
<211> LENGTH: 37
<212> TYPE: PRT
<213> ORGANISM: Hadronyche infensa

<400> SEQUENCE: 19

```
Asn Glu Cys Ile Arg Lys Trp Leu Ser Cys Val Asp Arg Lys Asn Asp
1               5                   10                  15

Cys Cys Glu Gly Leu Glu Cys Tyr Lys Arg Arg His Ser Phe Glu Val
            20                  25                  30

Cys Val Pro Ile Pro
        35
```

<210> SEQ ID NO 20
<211> LENGTH: 38
<212> TYPE: PRT
<213> ORGANISM: Hadronyche infensa

<400> SEQUENCE: 20

```
Asn Glu Cys Ile Arg Lys Trp Leu Ser Cys Val Asp Arg Lys Asn Asp
1               5                   10                  15

Cys Cys Glu Gly Leu Glu Cys Tyr Lys Arg Arg His Ser Phe Glu Val
            20                  25                  30

Cys Val Pro Ile Pro Gly
        35
```

<210> SEQ ID NO 21
<211> LENGTH: 40
<212> TYPE: PRT
<213> ORGANISM: Hadronyche infensa

<400> SEQUENCE: 21

```
Ile Pro Gly Phe Cys Leu Val Lys Trp Lys Gln Cys Asp Gly Arg Glu
1               5                   10                  15

Arg Asp Cys Cys Ala Gly Leu Glu Cys Trp Lys Arg Ser Gly Asn Lys
            20                  25                  30

Ser Ser Val Cys Ala Pro Ile Thr
        35                  40
```

<210> SEQ ID NO 22
<211> LENGTH: 76
<212> TYPE: PRT
<213> ORGANISM: Hadronyche infensa

<400> SEQUENCE: 22

```
Ser Asn Glu Cys Ile Arg Lys Trp Lys Ser Cys Val Asp Arg Lys Asn
1               5                   10                  15

Asp Cys Cys Glu Gly Leu Glu Cys Tyr Lys Arg Arg His Ser Phe Glu
            20                  25                  30

Val Cys Val Pro Ile Pro Gly Phe Cys Leu Val Lys Trp Lys Gln Cys
        35                  40                  45

Asp Gly Arg Glu Arg Asp Cys Cys Ala Gly Leu Glu Cys Trp Lys Arg
    50                  55                  60
```

```
Ser Gly Asn Lys Ser Ser Val Cys Ala Pro Ile Thr
 65                  70                  75

<210> SEQ ID NO 23
<211> LENGTH: 76
<212> TYPE: PRT
<213> ORGANISM: Hadronyche infensa

<400> SEQUENCE: 23

Ser Asn Glu Cys Ile Arg Lys Trp Leu Ser Cys Val Asp Arg Lys Asn
 1               5                  10                  15

Asp Cys Cys Glu Gly Leu Glu Cys Trp Lys Arg Arg His Ser Phe Glu
             20                  25                  30

Val Cys Val Pro Ile Pro Gly Phe Cys Leu Val Lys Trp Lys Gln Cys
         35                  40                  45

Asp Gly Arg Glu Arg Asp Cys Cys Ala Gly Leu Glu Cys Trp Lys Arg
     50                  55                  60

Ser Gly Asn Lys Ser Ser Val Cys Ala Pro Ile Thr
 65                  70                  75

<210> SEQ ID NO 24
<211> LENGTH: 76
<212> TYPE: PRT
<213> ORGANISM: Hadronyche infensa

<400> SEQUENCE: 24

Ser Asn Glu Cys Ile Arg Lys Trp Leu Ser Cys Val Asp Arg Lys Asn
 1               5                  10                  15

Asp Cys Cys Glu Gly Leu Glu Cys Tyr Lys Arg Arg Ser Phe Glu
             20                  25                  30

Val Cys Val Pro Ile Pro Gly Phe Cys Leu Val Lys Trp Lys Gln Cys
         35                  40                  45

Asp Gly Arg Glu Arg Asp Cys Cys Ala Gly Leu Glu Cys Trp Lys Arg
     50                  55                  60

Ser Gly Asn Lys Ser Ser Val Cys Ala Pro Ile Thr
 65                  70                  75

<210> SEQ ID NO 25
<211> LENGTH: 78
<212> TYPE: PRT
<213> ORGANISM: Engineered peptide

<400> SEQUENCE: 25

Ser Glu Asp Cys Ile Pro Lys Trp Lys Gly Cys Val Asn Arg His Gly
 1               5                  10                  15

Asp Cys Cys Glu Gly Leu Glu Cys Trp Lys Arg Arg Ser Phe Glu
             20                  25                  30

Val Cys Val Pro Lys Thr Glu Asp Cys Ile Pro Lys Trp Lys Gly Cys
         35                  40                  45

Val Asn Arg His Gly Asp Cys Cys Glu Gly Leu Glu Cys Trp Lys Arg
     50                  55                  60

Arg Arg Ser Phe Glu Val Cys Val Pro Lys Thr Pro Lys Thr
 65                  70                  75

<210> SEQ ID NO 26
<211> LENGTH: 78
<212> TYPE: PRT
<213> ORGANISM: Engineered peptide
```

```
<400> SEQUENCE: 26

Ser Glu Asp Cys Ile Pro Lys Trp Lys Gly Cys Val Asn Arg His Gly
1               5                   10                  15

Asp Cys Cys Glu Gly Leu Glu Cys Trp Lys Arg Arg Ser Phe Glu
            20                  25                  30

Val Cys Val Pro Lys Thr Gly Asp Cys Ile Pro Lys Trp Lys Gly Cys
            35                  40                  45

Val Asn Arg His Gly Asp Cys Cys Glu Gly Leu Glu Cys Trp Lys Arg
        50                  55                  60

Arg Arg Ser Phe Glu Val Cys Val Pro Lys Thr Pro Lys Thr
65                  70                  75

<210> SEQ ID NO 27
<211> LENGTH: 79
<212> TYPE: PRT
<213> ORGANISM: Engineered peptide

<400> SEQUENCE: 27

Ser Asn Glu Cys Ile Arg Lys Trp Leu Ser Cys Val Asp Arg Lys Asn
1               5                   10                  15

Asp Cys Cys Glu Gly Leu Glu Cys Tyr Lys Arg Arg His Ser Phe Glu
            20                  25                  30

Val Cys Val Pro Gly Gly Gly Gly Gly Phe Cys Leu Val Lys Trp
            35                  40                  45

Lys Gln Cys Asp Gly Arg Glu Arg Asp Cys Cys Ala Gly Leu Glu Cys
        50                  55                  60

Trp Lys Arg Ser Gly Asn Lys Ser Ser Val Cys Ala Pro Ile Thr
65                  70                  75

<210> SEQ ID NO 28
<211> LENGTH: 81
<212> TYPE: PRT
<213> ORGANISM: Engineered peptide

<400> SEQUENCE: 28

Ser Glu Asp Cys Ile Pro Lys Trp Lys Gly Cys Val Asn Arg His Gly
1               5                   10                  15

Asp Cys Cys Glu Gly Leu Glu Cys Trp Lys Arg Arg Ser Phe Glu
            20                  25                  30

Val Cys Val Pro Lys Thr Pro Lys Thr Ile Pro Gly Phe Cys Leu Val
            35                  40                  45

Lys Trp Lys Gln Cys Asp Gly Arg Glu Arg Asp Cys Cys Ala Gly Leu
        50                  55                  60

Glu Cys Trp Lys Arg Ser Gly Asn Lys Ser Ser Val Cys Ala Pro Ile
65                  70                  75                  80

Thr

<210> SEQ ID NO 29
<211> LENGTH: 75
<212> TYPE: PRT
<213> ORGANISM: Hadronyche infensa

<400> SEQUENCE: 29

Asn Glu Cys Ile Arg Lys Trp Leu Ser Cys Val Asp Arg Lys Asn Asp
1               5                   10                  15

Cys Cys Glu Gly Leu Glu Cys Tyr Lys Arg Arg His Ser Phe Glu Val
            20                  25                  30
```

```
Cys Val Pro Ile Pro Gly Phe Cys Leu Val Lys Trp Lys Gln Cys Asp
            35                  40                  45

Gly Arg Glu Arg Asp Cys Cys Pro Gly Leu Glu Cys Trp Lys Arg Ser
 50                  55                  60

Gly Asn Lys Ser Ser Val Cys Ala Pro Ile Thr
 65                  70                  75
```

<210> SEQ ID NO 30
<211> LENGTH: 100
<212> TYPE: PRT
<213> ORGANISM: Hadronyche infensa

<400> SEQUENCE: 30

```
Gln Glu Cys Ile Ala Lys Trp Lys Ser Cys Ala Gly Arg Lys Leu Asp
 1               5                  10                  15

Cys Cys Glu Gly Leu Glu Cys Trp Lys Arg Arg Trp Gly His Glu Val
            20                  25                  30

Cys Val Pro Ile Thr Gln Lys Ile Leu Leu Phe Arg Lys Val Glu Lys
            35                  40                  45

Ser Cys Phe Glu Arg Lys Tyr Asp Cys Cys Glu Glu Leu Glu Cys Trp
 50                  55                  60

Glu Arg Arg Gly Asn Lys Thr Pro Ser Met Arg Thr Lys Ala Val Arg
 65                  70                  75                  80

Ser Val Ser Gly His Glu Ala Leu Ser Val Ala Leu Leu Lys Thr Cys
                85                  90                  95

Ile His Tyr Lys
            100
```

<210> SEQ ID NO 31
<211> LENGTH: 77
<212> TYPE: PRT
<213> ORGANISM: Hadronyche infensa

<400> SEQUENCE: 31

```
Gln Glu Cys Ile Ala Lys Trp Lys Ser Cys Ala Gly Arg Lys Leu Asp
 1               5                  10                  15

Cys Cys Glu Gly Leu Glu

```
    50                  55                  60

Gly Asn Lys Ser Ser Val Cys Ala Pro Ile Ala
65                  70                  75

<210> SEQ ID NO 33
<211> LENGTH: 75
<212> TYPE: PRT
<213> ORGANISM: Hadronyche infensa

<400> SEQUENCE: 33

Asn Glu Cys Ile Arg Lys Trp Leu Ser Cys Val Asp Arg Lys Asn Asp
1               5                   10                  15

Cys Cys Glu Gly Leu Glu Cys Tyr Lys Arg Arg His Ser Phe Glu Val
            20                  25                  30

Cys Val Pro Ile Pro Gly Phe Cys Leu Val Lys Trp Lys Gln Cys Asp
        35                  40                  45

Gly Arg Glu Arg Asp Cys Cys Ala Gly Leu Glu Cys Trp Lys Arg Ser
    50                  55                  60

Gly Asn Lys Ser Ser Val Cys Ala Pro Ile Ala
65                  70                  75

<210> SEQ ID NO 34
<211> LENGTH: 1416
<212> TYPE: DNA
<213> ORGANISM: Artificial sequence
<220> FEATURE:
<223> OTHER INFORMATION: Coding sequence for recombinant Hi1a

<400> SEQUENCE: 34
atgatgtttt ccgcctcggc tctcgccaaa atccatcacc atcaccatca cgaagaaggt      60
aaactggtaa tctggattaa cggcgataaa ggctataacg gtctcgctga agtcggtaag     120
aaattcgaga aagataccgg aattaaagtc accgttgagc atccggataa actggaagag     180
aaattcccac aggttgcggc aactggcgat ggccctgaca ttatcttctg ggcacacgac     240
cgctttggtg gctacgctca atctggcctg ttggctgaaa tcaccccgga caaagcgttc     300
caggacaagc tgtatccgtt tacctgggat gccgtacgtt acaacggcaa gctgattgct     360
tacccgatcg ctgttgaagc gttatcgctg atttataaca aagatctgct gccgaacccg     420
ccaaaaacct gggaagagat cccggcgctg gataaagaac tgaaagcgaa aggtaagagc     480
gcgctgatgt tcaacctgca agaaccgtac ttcacctggc cgctgattgc tgctgacggg     540
ggttatgcgt tcaagtatga aaacggcaag tacgacatta aagacgtggg cgtggataac     600
gctggcgcga aagcgggtct gaccttcctg gttgacctga ttaaaaacaa acacatgaat     660
gcagacaccg attactccat cgcagaagct gcctttaata aaggcgaaac agcgatgacc     720
atcaacggcc cgtgggcatg gtccaacatc gacaccagca aagtgaatta tggtgtaacg     780
gtactgccga ccttcaaggg tcaaccatcc aaaccgttcg ttggcgtgct gagcgcaggt     840
attaacgccg ccagtccgaa caaagagctg gcaaaagagt tcctcgaaaa ctatctgctg     900
actgatgaag gtctggaagc ggttaataaa gacaaaccgc tgggtgccgt agcgctgaag     960
tcttacgagg aagagttggc gaaagatcca cgtattgccg ccaccatgga aaacgcccag    1020
aaaggtgaaa tcatgccgaa catcccgcag atgtccgctt tctggtatgc cgtgcgtact    1080
gcggtgatca acgccgccag cggtcgtcag actgtcgatg aagccctgaa agacgcgcag    1140
actgattacg atatcccagg taccgaaaac ctgtattttc agagcaatga atgcattcgt    1200
aaatggctga gctgcgttga tcgtaaaaat gattgttgtg aaggcctgga atgctataaa    1260
```

```
cgtcgtcata gctttgaagt tgtgttccg attccgggtt tttgtctggt taaatggaaa    1320
cagtgtgatg gtcgtgaacg tgattgctgt gccggtctgg aatgttggaa acgtagcggt    1380
aataaaagca gcgtttgtgc accgatcacc taataa                              1416
```

<210> SEQ ID NO 35
<211> LENGTH: 470
<212> TYPE: PRT
<213> ORGANISM: Artificial sequence
<220> FEATURE:
<223> OTHER INFORMATION: Full precursor for recombinant Hi1a

<400> SEQUENCE: 35

```
Met Met Phe Ser Ala Ser Ala Leu Ala Lys Ile His His His His
1               5                   10                  15

His Glu Glu Gly Lys Leu Val Ile Trp Ile Asn Gly Asp Lys Gly Tyr
            20                  25                  30

Asn Gly Leu Ala Glu Val Gly Lys Lys Phe Glu Lys Asp Thr Gly Ile
        35                  40                  45

Lys Val Thr Val Glu His Pro Asp Lys Leu Glu Glu Lys Phe Pro Gln
    50                  55                  60

Val Ala Ala Thr Gly Asp Gly Pro Asp Ile Ile Phe Trp Ala His Asp
65                  70                  75                  80

Arg Phe Gly Gly Tyr Ala Gln Ser Gly Leu Leu Ala Glu Ile Thr Pro
                85                  90                  95

Asp Lys Ala Phe Gln Asp Lys Leu Tyr Pro Phe Thr Trp Asp Ala Val
            100                 105                 110

Arg Tyr Asn Gly Lys Leu Ile Ala Tyr Pro Ile Ala Val Glu Ala Leu
        115                 120                 125

Ser Leu Ile Tyr Asn Lys Asp Leu Leu Pro Asn Pro Pro Lys Thr Trp
    130                 135                 140

Glu Glu Ile Pro Ala Leu Asp Lys Glu Leu Lys Ala Lys Gly Lys Ser
145                 150                 155                 160

Ala Leu Met Phe Asn Leu Gln Glu Pro Tyr Phe Thr Trp Pro Leu Ile
                165                 170                 175

Ala Ala Asp Gly Gly Tyr Ala Phe Lys Tyr Glu Asn Gly Lys Tyr Asp
            180                 185                 190

Ile Lys Asp Val Gly Val Asp Asn Ala Gly Ala Lys Ala Gly Leu Thr
        195                 200                 205

Phe Leu Val Asp Leu Ile Lys Asn Lys His Met Asn Ala Asp Thr Asp
    210                 215                 220

Tyr Ser Ile Ala Glu Ala Ala Phe Asn Lys Gly Glu Thr Ala Met Thr
225                 230                 235                 240

Ile Asn Gly Pro Trp Ala Trp Ser Asn Ile Asp Thr Ser Lys Val Asn
                245                 250                 255

Tyr Gly Val Thr Val Leu Pro Thr Phe Lys Gly Gln Pro Ser Lys Pro
            260                 265                 270

Phe Val Gly Val Leu Ser Ala Gly Ile Asn Ala Ala Ser Pro Asn Lys
        275                 280                 285

Glu Leu Ala Lys Glu Phe Leu Glu Asn Tyr Leu Leu Thr Asp Glu Gly
    290                 295                 300

Leu Glu Ala Val Asn Lys Asp Lys Pro Leu Gly Ala Val Ala Leu Lys
305                 310                 315                 320

Ser Tyr Glu Glu Glu Leu Ala Lys Asp Pro Arg Ile Ala Ala Thr Met
                325                 330                 335
```

-continued

Glu Asn Ala Gln Lys Gly Glu Ile Met Pro Asn Ile Pro Gln Met Ser
            340                 345                 350

Ala Phe Trp Tyr Ala Val Arg Thr Ala Val Ile Asn Ala Ala Ser Gly
            355                 360                 365

Arg Gln Thr Val Asp Glu Ala Leu Lys Asp Ala Gln Thr Asp Tyr Asp
            370                 375                 380

Ile Pro Gly Thr Glu Asn Leu Tyr Phe Gln Ser Asn Glu Cys Ile Arg
385                 390                 395                 400

Lys Trp Leu Ser Cys Val Asp Arg Lys Asn Asp Cys Cys Glu Gly Leu
            405                 410                 415

Glu Cys Tyr Lys Arg Arg His Ser Phe Glu Val Cys Val Pro Ile Pro
            420                 425                 430

Gly Phe Cys Leu Val Lys Trp Lys Gln Cys Asp Gly Arg Glu Arg Asp
            435                 440                 445

Cys Cys Ala Gly Leu Glu Cys Trp Lys Arg Ser Gly Asn Lys Ser Ser
            450                 455                 460

Val Cys Ala Pro Ile Thr
465                 470

<210> SEQ ID NO 36
<211> LENGTH: 38
<212> TYPE: PRT
<213> ORGANISM: Hadronyche infensa

<400> SEQUENCE: 36

Gly Phe Cys Leu Val Lys Trp Lys Gln Cys Asp Gly Arg Glu
1               5                   10

Arg Asp Cys Cys Ala Gly Leu Glu Cys Trp Lys Arg Ser Gly Asn Lys
15                  20                  25                  30

Ser Ser Val Cys Ala Pro Ile Thr
                35

<210> SEQ ID NO 37
<211> LENGTH: 77
<212> TYPE: PRT
<213> ORGANISM: Engineered peptide

<400> SEQUENCE: 37

Glu Asp Cys Ile Pro Lys Trp Lys Gly Cys Val Asn Arg His Gly
1               5                   10                  15

Asp Cys Cys Glu Gly Leu Glu Cys Trp Lys Arg Arg Ser Phe Glu
                20                  25                  30

Val Cys Val Pro Lys Thr Glu Asp Cys Ile Pro Lys Trp Lys Gly Cys
            35                  40                  45

Val Asn Arg His Gly Asp Cys Cys Glu Gly Leu Glu Cys Trp Lys Arg
            50                  55                  60

Arg Ser Phe Glu Val Cys Val Pro Lys Thr Pro Lys Thr
65                  70                  75

<210> SEQ ID NO 38
<211> LENGTH: 77
<212> TYPE: PRT
<213> ORGANISM: Engineered peptide

<400> SEQUENCE: 38

Glu Asp Cys Ile Pro Lys Trp Lys Gly Cys Val Asn Arg His Gly
1               5                   10                  15

```
Asp Cys Cys Glu Gly Leu Glu Cys Trp Lys Arg Arg Ser Phe Glu
            20                  25                  30

Val Cys Val Pro Lys Thr Gly Asp Cys Ile Pro Lys Trp Lys Gly Cys
            35                  40                  45

Val Asn Arg His Gly Asp Cys Cys Glu Gly Leu Glu Cys Trp Lys Arg
        50                  55                  60

Arg Arg Ser Phe Glu Val Cys Val Pro Lys Thr Pro Lys Thr
65                  70                  75
```

<210> SEQ ID NO 39
<211> LENGTH: 78
<212> TYPE: PRT
<213> ORGANISM: Engineered peptide

<400> SEQUENCE: 39

```
Asn Glu Cys Ile Arg Lys Trp Leu Ser Cys Val Asp Arg Lys Asn
1               5                   10                  15

Asp Cys Cys Glu Gly Leu Glu Cys Tyr Lys Arg Arg His Ser Phe Glu
            20                  25                  30

Val Cys Val Pro Gly Gly Gly Gly Gly Phe Cys Leu Val Lys Trp
            35                  40                  45

Lys Gln Cys Asp Gly Arg Glu Arg Asp Cys Cys Ala Gly Leu Glu Cys
        50                  55                  60

Trp Lys Arg Ser Gly Asn Lys Ser Ser Val Cys Ala Pro Ile Thr
65                  70                  75
```

<210> SEQ ID NO 40
<211> LENGTH: 80
<212> TYPE: PRT
<213> ORGANISM: Engineered peptide

<400> SEQUENCE: 40

```
Glu Asp Cys Ile Pro Lys Trp Lys Gly Cys Val Asn Arg His Gly
1               5                   10                  15

Asp Cys Cys Glu Gly Leu Glu Cys Trp Lys Arg Arg Ser Phe Glu
            20                  25                  30

Val Cys Val Pro Lys Thr Pro Lys Thr Ile Pro Gly Phe Cys Leu Val
            35                  40                  45

Lys Trp Lys Gln Cys Asp Gly Arg Glu Arg Asp Cys Cys Ala Gly Leu
        50                  55                  60

Glu Cys Trp Lys Arg Ser Gly Asn Lys Ser Ser Val Cys Ala Pro Ile
65                  70                  75

Thr
        80
```

<210> SEQ ID NO 41
<211> LENGTH: 8
<212> TYPE: PRT
<213> ORGANISM: Hadronyche infensa

<400> SEQUENCE: 41

```
Val Pro Ile Thr Gln Lys Ile Phe
1               5
```

```
<210> SEQ ID NO 42
<211> LENGTH: 6
<212> TYPE: PRT
<213> ORGANISM: Hadronyche infensa

<400> SEQUENCE: 42

Val Pro Ile Pro Gly Phe
1               5
```